(12) United States Patent
Powell

(10) Patent No.: US 8,877,985 B2
(45) Date of Patent: *Nov. 4, 2014

(54) CO-PRODUCTION OF BIOFUELS AND GLYCOLS

(75) Inventor: Joseph Broun Powell, Houston, TX (US)

(73) Assignee: Shell Oil Company, Houston, TX (US)

( * ) Notice: Subject to any disclaimer, the term of this patent is extended or adjusted under 35 U.S.C. 154(b) by 8 days.

This patent is subject to a terminal disclaimer.

(21) Appl. No.: 13/495,705

(22) Filed: Jun. 13, 2012

(65) Prior Publication Data

US 2012/0323051 A1 Dec. 20, 2012

Related U.S. Application Data

(60) Provisional application No. 61/496,681, filed on Jun. 14, 2011.

(51) Int. Cl.
| | |
|---|---|
| *C07C 29/132* | (2006.01) |
| *C10G 3/00* | (2006.01) |
| *C07C 51/377* | (2006.01) |
| *C10L 1/04* | (2006.01) |
| *C07C 29/00* | (2006.01) |

(52) U.S. Cl.
CPC ............... *C10G 3/42* (2013.01); *C07C 29/132* (2013.01); *Y02T 50/678* (2013.01); *C10G 2300/1011* (2013.01); *C10G 3/00* (2013.01); *Y02E 50/13* (2013.01); *C07C 51/377* (2013.01); *C10G 2300/4081* (2013.01); *C10L 1/04* (2013.01); *C07C 29/00* (2013.01)
USPC ............ 568/863; 568/861; 568/868; 568/869

(58) Field of Classification Search
USPC .................................. 568/863, 861, 868, 869
See application file for complete search history.

(56) References Cited

U.S. PATENT DOCUMENTS

| | | | |
|---|---|---|---|
| 2008/0103340 A1* | 5/2008 | Binder et al. ................. 568/863 |
| 2008/0216391 A1* | 9/2008 | Cortright et al. ............... 44/307 |
| 2012/0000621 A1* | 1/2012 | Stigsson ....................... 162/158 |

* cited by examiner

*Primary Examiner* — Sudhakar Katakam
*Assistant Examiner* — Pancham Bakshi

(57) ABSTRACT

Methods and systems for co-producing higher hydrocarbons and glycols from bio-based feedstocks containing carbohydrates are disclosed.

25 Claims, 3 Drawing Sheets

US 8,877,985 B2

CO-PRODUCTION OF BIOFUELS AND GLYCOLS

The present application claims the benefit of U.S. Provisional Patent Application Ser. No. 61/496,681, filed Jun. 14, 2011 the entire disclosure of which is hereby incorporated by reference.

FIELD OF THE INVENTION

The invention relates to the production of higher hydrocarbons suitable for use in transportation fuels and industrial chemicals from bio-based feedstocks.

BACKGROUND OF THE INVENTION

A significant amount of effort has been placed on developing new methods and systems for providing energy from resources other than fossil fuels. Bio-based feedstocks are a resource that show promise as a renewable alternative source of hydrocarbons for producing fuel and chemicals.

Bio-based feedstocks including carbohydrates and "biomass" are materials derived from living or recently living biological materials. One type of biomass is cellulosic biomass. Cellulosic biomass is the most abundant source of carbohydrate in the world due to the lignocellulosic materials composing the cell walls. The ability to convert biomass to fuels, chemicals, energy and other materials is expected to strengthen the economy, minimize dependence on oil and gas resources, reduce air and water pollution, and decrease the net rate of carbon dioxide production.

There are many challenges to overcome in developing processes of converting carbohydrates to higher hydrocarbons suitable for use in transportation fuels. For example, the processes used are costly and complex making it difficult to compete with the use of traditional resources, such as fossil fuels. U.S. Patent Application Publication No. 2007/0142633 (Yao et al.) refers to a process for the conversion of carbohydrates to higher hydrocarbons. An ion-exchange resin is provided to convert the carbohydrates into usable reaction products. The reaction products are hydrogenated, and then contacted with a zeolite containing catalyst to form higher hydrocarbons. The conversion of carbohydrates to hydrocarbons in this system results in increased loss of desirable hydrocarbon products due to the formation of unwanted byproducts, such as coke, carbon dioxide, and carbon monoxide. Thus, another challenge for promoting and sustaining the use of biomass is the need to eliminate the formation of undesirable byproducts such as carbon monoxide, carbon dioxide, and coke. A further challenge is to complete the conversion of carbohydrates to higher hydrocarbons in a limited number of steps, to obtain high yields with minimal capital investment.

Current methods for converting sugars to fuel proceed through a biological route, such as yeast fermentation, to ethanol. However, ethanol does not have a high energy density when compared to standard transportation fuels. Currently, there is a need for the creation of liquid biofuels of greater energy density than ethanol, which can make use of existing fuel infrastructure. Moreover, what is needed is a method and system that provides efficient and high yield production of higher hydrocarbons suitable for use in transportation fuels and industrial chemicals from bio-based feedstocks while avoiding or minimizing the production of unwanted by-products.

Efficient conversion of carbohydrates to glycols such as ethylene glycol or propylene glycol at high yield for use as chemical products or intermediates, has been limited by the further reaction of glycols to monooxygenates and ultimately alkanes, such that high yields of glycols cannot be obtained at high conversions of the feed carbohydrates. Use of high temperatures to increase conversion in a single reaction step can also lead to heavy ends byproduct formation from carbohydrate feeds such as biomass or soluble sugars, due to reactivity of sugar intermediates to form caramelans and tars, prior to stabilization by hydrogen. Alternate use of low conversion at lower temperatures in a single reaction step requires separation and recycle of a large stream of unconverted carbohydrates, which increases processing costs for a process which targets only glycols as the principal commercial product. Low conversion to maximize glycol yields in a single reaction steps also results in the presence of unconverted feed carbohydrates including sugars and sugar alcohols, and polyoxygenated species containing more than three oxygens. These components cause excessive coke formation and deactivation of condensation-oligomerization catalyst, upon attempted processing of the monooxygenates-rich stream obtained after glycols separation, to liquid fuels.

SUMMARY OF THE INVENTION

An efficient process is provided which can produce a portion of glycols from carbohydrates without excessive heavy ends or light alkanes byproduct formation, and after separation of a glycol-rich stream, continue the processing for efficient conversion of a monooxygenates-rich stream to liquid fuels, to obtain high yields of glycols and liquid fuels, with minimal formation of heavy ends, tars, and light alkane (less than $C_5$) gaseous byproducts.

In an embodiment, a method comprises providing a bio-based feedstock stream containing carbohydrates and water; contacting, in a first reaction system, the bio-based feedstock stream with hydrogen in the presence of a hydrogenolysis catalyst at a temperature in the range of 120° C. to 280° C. and 0.1 to 150 bar of hydrogen to produce a hydrogenolysis stream containing at least 5 wt %, based on the total oxygenates content, of glycols that comprises ethylene glycol (EG) and 1,2-propylene glycol (PG), and other monooxygenates; contacting, in a second reaction system, at least a first portion of said hydrogenolysis stream with hydrogen in the presence of a hydrogenolysis catalyst at a temperature in the range of 160° C. to 280° C. and in the presence of 0.1 to 150 bar hydrogen to produce a oxygenated intermediate stream comprising at least 5 wt %, based on the total oxygenates, of monooxygenated hydrocarbons of chain length less than 6 carbons; processing at least a portion of the oxygenated intermediate stream to form a liquid fuel; providing a second portion of said hydrogenolysis stream to a first separation system; separating a portion of said hydrogenoloysis stream, in the first separation system, to a monooxygenates stream comprising monooxygenates and a glycol rich stream comprising at least 10 wt %, based on the total oxygenates, of glycols by flashing; and recovering glycols from the glycol rich stream.

In yet another embodiment, a method comprises providing a bio-based feedstock; contacting the bio-based feedstock with a digestive solvent to provide a bio-based feedstock stream containing carbohydrates and water; contacting, in a first reaction system, the bio-based feedstock stream with hydrogen in the presence of a hydrogenolysis catalyst at a temperature in the range of 120° C. to 280° C. and 0.1 to 150 bar of hydrogen to produce a hydrogenolysis stream containing at least 5 wt %, based on the total oxygenates content, of glycols that comprises ethylene glycol (EG) and 1,2-propylene glycol (PG), and other monooxygenates; contacting, in a second reaction system, at least a first portion of said hydrogenolysis stream with hydrogen in the presence of a hydrogenolysis catalyst at a temperature in the range of 160° C. to 280° C. and in the presence of 0.1 to 150 bar hydrogen to produce a oxygenated intermediate stream comprising at least 5 wt %, based on the total oxygenates, of monooxygenated hydrocarbons of chain length less than 6 carbons; processing at least a portion of the oxygenated intermediate stream to form a liquid fuel; providing a second portion of said hydrogenolysis stream to a first separation system; separating a portion of said hydrogenoloysis stream, in the first separation system, to a monooxygenates stream comprising monooxygenates and a glycol rich stream comprising at least 10 wt %, based on the total oxygenates, of glycols by flashing; and recovering glycols from the glycol rich stream.

In yet another embodiment, a method comprises providing a bio-based feedstock stream containing carbohydrates and water; contacting, in a first reaction zone, the bio-based feedstock stream with hydrogen in the presence of a hydrogenolysis catalyst at a temperature in the range of 120° C. to 280° C. and 0.1 to 150 bar of hydrogen to produce a hydrogenolysis intermediate containing at least 5 wt %, based on the total oxygenates content, of glycols that comprises ethylene glycol (EG) and 1,2-propylene glycol (PG), and other monooxygenates; contacting, in a second reaction zone, said hydrogenolysis intermediate with hydrogen in the presence of a hydrogenolysis catalyst at a temperature in the range of 160° C. to 280° C. and in the presence of 0.1 to 150 bar hydrogen to produce a combined glycol and oxygenated intermediate stream comprising at least 5 wt %, based on the total oxygenates, of monooxygenated hydrocarbons of chain length less than 6 carbons, and greater than 5 wt % glycols; separating, by flashing, the combined glycol and oxygenated intermediate stream into a glycol rich stream comprising at least 10 wt %, based on the total oxygenates, of glycols, and a monooxygenates-rich stream; processing at least a portion of the monooxygenates-rich stream to form a liquid fuel; and recovering glycols from the glycol rich stream.

BRIEF DESCRIPTION OF THE DRAWINGS

These drawings illustrate certain aspects of some of the embodiments of the invention, and should not be used to limit or define the invention.

DETAILED DESCRIPTION OF THE INVENTION

Figure 1:
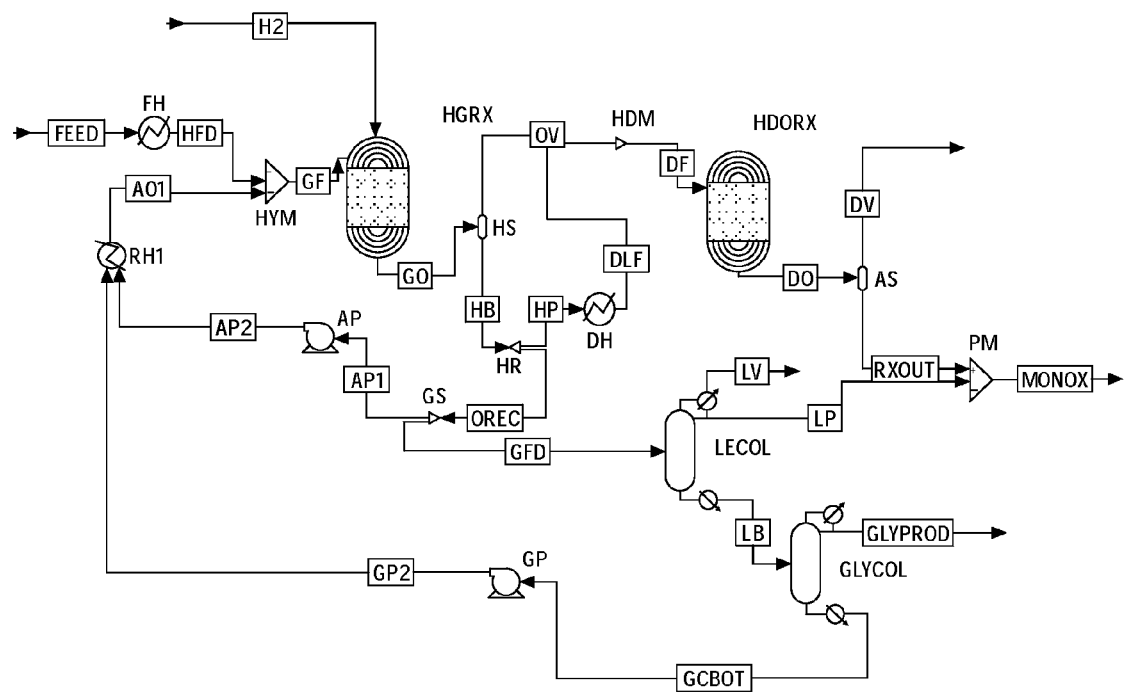
FIG. 1 is a process flow diagram of an embodiment of a biofuels and glycols production process of this invention.

The invention relates to methods and systems for producing higher hydrocarbons and glycols from bio-based feedstocks, such as carbohydrates, which include sugars, sugar alcohols, celluloses, lignocelluloses, hemicelluloses, lignocellulosic biomass, and any combination thereof, to form higher hydrocarbons suitable for use in transportation fuels and industrial chemicals, while minimizing the formation of undesirable by-products such as coke, carbon dioxide, and carbon monoxide. The higher hydrocarbons produced are useful in forming transportation fuels, such as synthetic gasoline, diesel fuel, and jet fuel, as well as industrial chemicals. The glycols produced are useful in many conventional chemicals applications as solvents and as chemical precursors. As used herein, the term "higher hydrocarbons" refers to hydrocarbons having an oxygen to carbon ratio less than at least one component of the bio-based feedstock. As used herein the term "hydrocarbon" refers to an organic compound comprising primarily hydrogen and carbon atoms, which is also an unsubstituted hydrocarbon. In certain embodiments, the hydrocarbons of the invention also comprise heteroatoms (e.g., oxygen or sulfur) and thus the term "hydrocarbon" may also include substituted hydrocarbons. The term "soluble carbohydrates" refers to oligosaccharides and monosaccharides that are soluble in the digestive solvent and that can be used as feedstock to the hydrogenolysis reaction (e.g., pentoses and hexoses).

In an embodiment, the reactions described below are carried out in any system of suitable design, including systems comprising continuous-flow, batch, semi-batch, or multi-system vessels and reactors. One or more reactions may take place in an individual vessel and the process is not limited to separate reaction vessels for each reaction. In an embodiment, the invention utilizes a fixed or fluidized catalytic bed system. Preferably, the invention is practiced using a continuous-flow system at steady-state.

The methods and systems of the invention have the advantage of converting bio-based feedstocks, optionally without any additional costly purification steps to form higher energy density product of lower oxygen/carbon ratio including higher alkanes, olefins, and aromatics. Another advantage of the present invention includes the fact that glycol coproducts are readily produced as intermediates and easily separated by flash distillation from the primarily mono-oxygenate intermediates used to produce liquid biofuels by condensation or oligomerization reactions.

While not intending to be limited by theory, it is believed that some carbohydrates may thermally degrade at the conditions needed to produce higher hydrocarbons. In addition, the inclusion of some higher polyols in a reaction to form high hydrocarbons can result in formation of tars or coke. As an advantage of the present process, smaller reactor volumes and catalyst charges can be employed to only partially convert carbohydrate feeds to a mixture of primarily polyols including glycols and monooxygenates, as it is not necessary to drive the reactions to complete conversion of carbohydrates, in order to protect condensation-oligomerization catalysts used in subsequent steps, from excessive coke and tar formation. Unreacted carbohydrates and polyols including glycols are easily separated by flash distillation, and recycled back to the aqueous phase reforming reactor. Advantages of specific embodiments will be described in more detail below.

An embodiment of the invention comprises (i) providing bio-based feedstock stream containing carbohydrates and water; (ii) contacting the bio-based feedstock stream with hydrogen in the presence of a hydrogenolysis catalyst, in the first reaction system, at a temperature in the range of 120° C. to 280° C. and 0.1 to 150 bar of hydrogen to produce a hydrogenolysis stream containing at least 5 wt %, preferably 10 wt %, more preferably 20 wt %, based on the total oxygenates content, of glycols that comprises ethylene glycol (EG) and 1,2-propylene glycol (PG), and other monooxygenates; (iii) contacting at least a first portion of said hydrogenolysis stream to a second reaction system comprising a hydrogenolysis catalyst at a temperature in the range of 160° C. to 280° C. and in the presence of 0.1 to 150 bar hydrogen to produce a oxygenated intermediate stream comprising of 5 wt %, preferably 10 wt %, more preferably 15 wt % based on the total oxygenates, of monooxygenated hydrocarbons of chain length less than 6 carbons; (iv) processing at least a portion of the oxygenated intermediates to form a liquid fuel; (v) providing a second portion of said hydrogenolysis stream to a first separation system; (vi) separating a portion of said hydrogenolysis stream, in the first separation system, to a monooxygenates-rich stream comprising monooxygenates, polyols including some glycols, alkanes, and water, and a glycol rich stream comprising at least 10 wt %, preferably 15 wt %, more preferably 20 wt %, most preferably 25 wt %, based on the total oxygenates content, of glycols by flashing; (vii) recovering glycols from the glycol rich stream; and (vii) optionally recycling said monooxygenates-rich stream to the first reaction system. The ratio of the hydrogenolysis stream provided to the first separation system to the second reaction system is in the range of 1.5:1 to 10:1. At least a portion of the monooxygenates stream from the processing system and at least a portion of the monooxygenates stream from the first separation system may be recycled to the first reaction system to digest biomass to produce the aqueous carbohydrate feed.

Use of separate processing zones for steps (ii) and (iii) allows conditions to be optimized for digestion and hydrogenation or hydrogenolysis of the digested biomass components, independent from optimization of the conversion of oxygenated intermediates to the monooxygenates-rich stream comprising monooxygenates as well as some polyols and alkanes in addition to water, before feeding to step (iv) to make higher hydrocarbon fuels. A lower reaction temperature in step (iii) may be advantageous to minimize heavy ends byproduct formation, by conducting the hydrogenation and hydrogenolysis steps initially at a low temperature, whereby sugar molecules formed upon hydrolysis of carbohydrate feeds, are stabilized by hydrogenation to avoid formation of caramelans and tars. This has been observed to result in an intermediates stream which is rich in diols and polyols, but essentially free of heavy ends and non-hydrogenated monosaccharides which otherwise would serve as heavy ends precursors. The subsequent conversion of mostly solubilized and hydrogenated intermediates can be done efficiently in a second reaction zone at a higher temperature, optionally with an alternate catalyst optimized for production of monooxygenated hydrocarbons suitable for processing to liquid fuels, where residence time is minimized to avoid the undesired continued reaction of monooxygenates to form light alkane or alkene byproducts. Effective choice of catalyst can minimize the formation of light alkanes of carbon number less than five, which are not useful as liquid fuels. In this manner, overall yields to desired glycols and monooxygenates-rich streams may be improved, via conducting the conversion in two or more stages.

Figure 2:
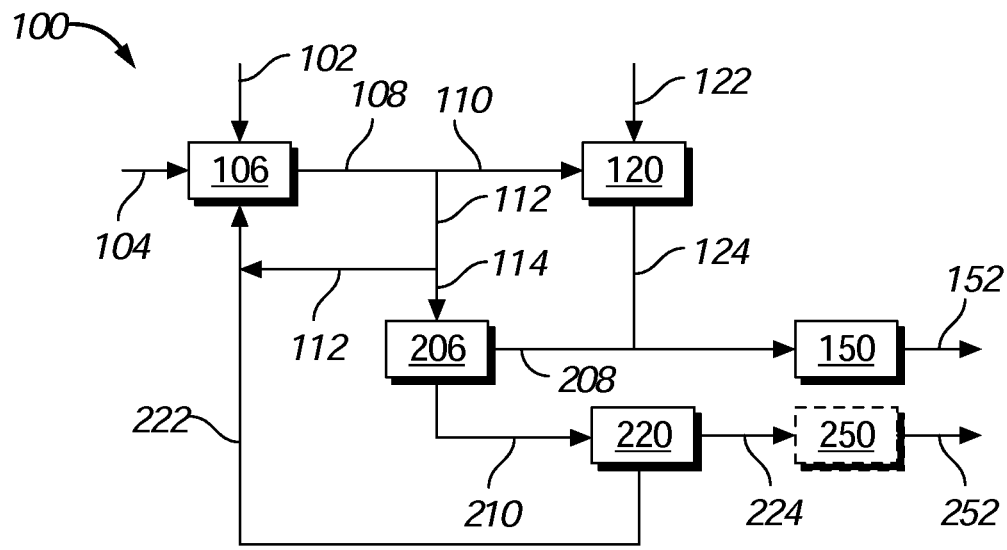
FIG. 2 schematically illustrates a block flow diagram of an embodiment of a biofuels and glycols production process of this invention.
Figure 3:
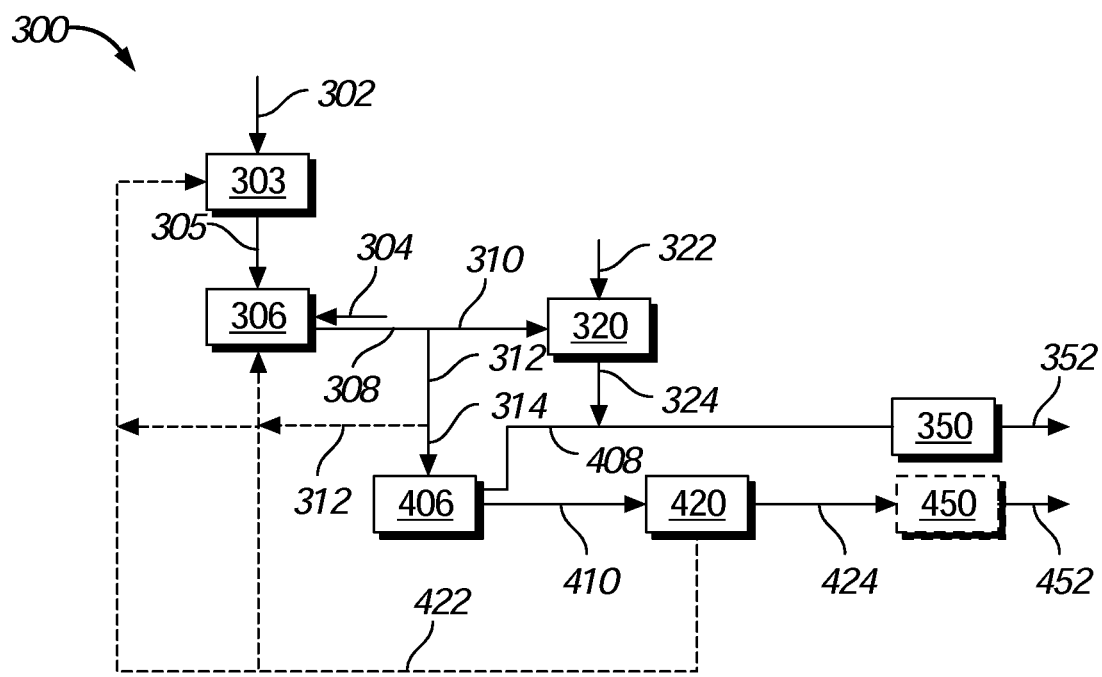
FIG. 3 schematically illustrates a block flow diagram of another embodiment of a biofuels and glycols production process of this invention.
Figure 4:
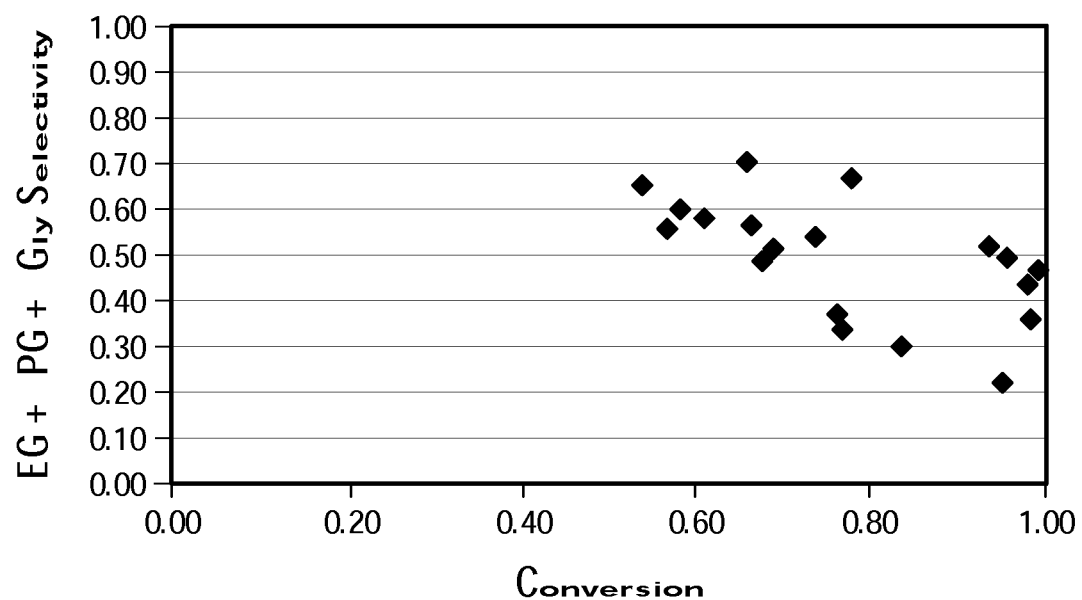
FIG. 4 shows a cross plot of conversion of sorbitol, vs. selectivity to glycols including glycerol.

FIG. 2 illustrates an embodiment of a process 100 according to the present invention. Another embodiment is illustrated in FIG. 3. FIG. 1 is a process flow diagram of one embodiment of such process. FIG. 4 describes yield of glycols including glycerol vs. conversion of sorbitol, for typical catalysts used with this invention.

In reference to FIG. 2, in one embodiment of the invention process 100, bio-based feedstock stream containing carbohydrates and water 102 from biomass is provided to a hydrogenolysis system (first reaction system or zone) 106 containing a hydrogenolysis catalyst whereby the carbohydrate is catalytically reacted with hydrogen 104 in the presence of a hydrogenolysis catalyst at a temperature in the range of 120° C. to 280° C. and in the range of 0.1 to 150 bar of hydrogen to produce a hydrogenolysis stream containing at least 5 wt %, preferably at least 10 wt % based on the total oxygenates content, of glycols, that comprises ethylene glycol (EG) and 1,2-propylene glycol (PG), and other monooxygenates 108, and at least a first portion of the hydrogenolysis stream 110 is provided to a second reaction system (or zone) 120 containing a hydrogenolysis catalyst whereby the hydrogenolysis stream is catalytically reacted with hydrogen 122 at a temperature in the range of 160° C. to 280° C. and in the range of 0.1 to 150 bar hydrogen to produce an oxygenated intermediate stream 124 containing at least 5 wt %, based on the total oxygenates content, of monooxygenated hydrocarbons of chain length less than 6 carbons. Then at least a portion of the oxygenated intermediate stream 124 is provided to a processing system 150 to produce higher hydrocarbons to form a liquid fuel 152. A portion of a second portion of the hydrogenolysis stream 112 is optionally provided as a recycle stream to the hydrogenolysis system. A second portion of the hydrogenolysis stream 114 is provided to a first separation system 206 such as a light ends column, that removes a small portion of monooxygenates formed in the hydrogenolysis system with water by flashing to provide a glycol enriched stream 210 and monooxygenates-rich stream 208. The glycol enriched stream as a second portion (bottoms) from the first separation system is provided to a second separation system 220, a polyols recovery column, where EG and PG are separated overhead as glycol stream 224 and heavier stream containing heavier glycols and unconverted carbohydrates (sorbitol) are recycled back to the feed 102 or hydrogenolysis system 106. The glycol stream may further be finished in a further third separation column 250 to produce finished EG, PG or a mixture of EG and PG product(s) 252. Monooxygenates-rich stream 208 is also fed to processing system 150 to produce higher hydrocarbons and aromatics to form a liquid fuel.

Oxygenated intermediate stream 124 and monooxygenates-rich stream 208 (monooxygenates solvent streams) may optionally be used to provide solvent to digest biomass to produce bio-based feedstock stream 102. In one embodiment, the oxygenated intermediate stream from the second reaction system may be flash distilled to provide a stream containing at least a portion of monooxygenate intermediates, and optionally a portion of the glycols, as feed for production of liquid fuels. Further, the bottoms from flashing containing enriched concentrations of unconverted carbohydrates, sugar alcohols, glycols, and some monooxygenates, may be recycle to the first reaction system.

In reference to FIG. 3, in one embodiment of the invention process 300, bio-based feedstock 302 from biomass is provided to a digestion system 303 that may have one or more digester(s), whereby the biomass is contacted with a digestive solvent. The digestive solvent is optionally at least a portion recycled from the hydrogenolysis reaction as a recycle stream. The hydrogenolysis recycle stream can comprise a number of components including in situ generated solvents, which may be useful as digestive solvent at least in part or in entirety. The term "in situ" as used herein refers to a component that is produced within the overall process; it is not limited to a particular reactor for production or use and is therefore synonymous with an in-process generated component. The in situ generated solvents may comprise oxygenated intermediates. The non-extractable solids may be removed from the reaction as an outlet stream. The treated bio-based feedstock stream 305 is an intermediate stream that may comprise the treated biomass at least in part in the form of soluble carbohydrates and water. The composition of the treated bio-based feedstock stream 305 may vary and may comprise a number of different compounds. Preferably, the contained carbohydrates will have 2 to 12 carbon atoms, and even more preferably 2 to 6 carbon atoms. The carbohydrates may also have an oxygen to carbon ratio from 0.5:1 to 1:1.2. Oligomeric carbohydrates containing more than 12 carbon atoms may also be present. At least a portion of the treated bio-based feedstock stream is provided to a hydrogenolysis system (first reaction system or zone) 306 containing a hydrogenolysis catalyst whereby the carbohydrate is catalytically reacted with hydrogen 304 in the presence of a hydrogenolysis catalyst at a temperature in the range of 120° C. to 280° C. and in the range of 0.1 to 150 bar of hydrogen to produce a hydrogenolysis stream containing at least 5 wt %, preferably at least 10 wt % based on the total oxygenates content, of glycols, that comprises ethylene glycol (EG) and 1,2-propylene glycol (PG), and other monooxygenates 308, and at least a first portion of the hydrogenolysis stream 310 is provided to a second reaction system (or zone) 320 containing a hydrogenolysis catalyst whereby the hydrogenolysis stream is catalytically reacted with hydrogen 322 at a temperature in the range of 160° C. to 280° C. and in the range of 0.1 to 150 bar hydrogen to produce a oxygenated intermediate stream 324 containing at least 5 wt %, based on the total oxygenates content, of monooxygenated hydrocarbons of chain length less than 6 carbons. Then at least a portion of the oxygenated intermediate stream 324 is provided to a processing system 350 to produce higher hydrocarbons to form a liquid fuel 352. A portion of a second portion of the hydrogenolysis stream 312 may optionally be provided as a recycle stream to the hydrogenolysis system or digestion system. A second portion of the hydrogenolysis stream 314 is provided to a first separation system 406 such as a light ends column, that removes a small portion of monooxygenates formed in the hydrogenolysis system with water by flashing to provide a glycol enriched stream 410 and monooxygenates stream 408. The glycol enriched stream as a second portion (bottoms) from the first separation system is provided to a second separation system 420, a polyols recovery column, where EG and PG are separated overhead as glycol stream 424 and heavier stream containing heavier glycols and unconverted carbohydrates (sorbitol) are recycled back to the feed 302 or digestion system 303 or hydrogenolysis system 306. The glycol stream may further be finished in a further third separation column 450 to produce finished EG, PG or a mixture of EG and PG product(s) 452. Monooxygenates stream 408 may also fed to processing system 350 to produce higher hydrocarbons and aromatics to form a liquid fuel. Oxygenated intermediate stream 324 and monooxygenates stream 408 (monooxygenates solvent streams) may optionally be used to provide solvent to digest biomass as recycle stream. A combined stream 324 and 408 may be flashed to produce an overhead solvent concentrate for recycle. The treated bio-based feedstock stream 305 may be optionally washed prior to feeding to the hydrogenolysis system (or zone) 306. If washed, water is most typically used as wash solvent. The digestion system 303 and the hydrogenolysis system (or zone) 306 may be carried out in a separate or the same reactor.

In another embodiment (not shown), hydrogenolysis intermediate from a first reaction zone is routed in its entirety to a second reaction zone operating at a temperature at least ten degrees Celsius higher than the first reaction zone to produce a combined glycol and monooxygenates-rich stream. The reaction zones may comprise two zones within a single reactor. A portion of ethylene glycol and propylene glycol are recovered from the combined stream, and at least a portion of the monooxygenates-rich stream is processed into liquid fuels. Optionally, either or both of the glycols rich stream or monooxygenates stream are recycled as solvent to the first reaction zone, or optionally to a digester to solubilize biomass or bio-based feeds for supply to the first reaction zone In yet another embodiment, providing a bio-based feedstock stream containing carbohydrates and water, contacting, in a first reaction zone, the bio-based feedstock stream with hydrogen in the presence of a hydrogenolysis catalyst at a temperature in the range of 120° C. to 280° C. and 0.1 to 150 bar of hydrogen to produce a hydrogenolysis intermediate containing at least 5 wt %, based on the total organics content, of glycols comprising ethylene glycol (EG) and 1,2-propylene glycol (PG), and other organics; routing the hydrogenolysis intermediate with glycols to a second reaction zone operating at a temperature at least 10° C. higher than the first reaction zone, separating at least a portion of said monooxygenates and glycol stream by flashing, to a glycol rich stream comprising at least 10 wt %, based on the total organics, of glycols and a monooxygenates-rich stream comprising other organics and water; optionally recycling a portion of either or both of the glycols rich stream or monooxygenates-rich stream to serve as solvent for the initial reaction step, processing at least a portion of the monooxygenates-rich stream to form a liquid fuel; and recovering glycols from the glycol rich stream. The recycled solvent stream may be optionally recycled to a digester, to provide digested biomass-feed for the initial reaction zone.

In an embodiment, the carbohydrates fed to the process as bio-based feedstock stream may be derived from an organic source (e.g., sugars and starches from corn or sugarcane). In another embodiment, the bio-based feedstock streams are derived from bio-based feedstocks. Bio-based feedstocks can include biomass. As used herein, the term "biomass" means organic materials produced by plants (e.g., leaves, roots, seeds and stalks), and microbial and animal metabolic wastes. Common sources of biomass include: agricultural wastes (e.g., corn stalks, straw, seed hulls, sugarcane leavings, bagasse, nutshells, and manure from cattle, poultry, and hogs); wood materials (e.g., wood or bark, sawdust, timber slash, and mill scrap); municipal waste, (e.g., waste paper and yard clippings); and energy crops, (e.g., poplars, willows, switch grass, alfalfa, prairie bluestream, corn, and soybean). The term "biomass" also refers to the primary building blocks of all the above, including, but not limited to, saccharides, lignins, celluloses, hemicelluloses, and starches. Any suitable (e.g., inexpensive and/or readily available) type of biomass can be used. Suitable lignocellulosic biomass can be, for example, selected from, but not limited to, forestry residues, agricultural residues, herbaceous material, municipal solid wastes, waste and recycled paper, pulp and paper mill residues, and combinations thereof. Thus, in some embodiments, the biomass can comprise, for example, corn stover, straw, bagasse, miscanthus, sorghum residue, switch grass, bamboo, water hyacinth, hardwood, hardwood chips, hardwood pulp, softwood, softwood chips, softwood pulp, and/or combination of these feedstocks. The biomass can be chosen based upon a consideration such as, but not limited to, cellulose and/or hemicelluloses content, lignin content, growing time/season, growing location/transportation cost, growing costs, harvesting costs and the like. Plant materials store carbohydrates either as sugars, starches, celluloses, lignocelluloses, hemicelluloses, and any combination thereof. In one embodiment, the carbohydrates include monosaccharides, polysaccharides or mixtures of monosaccharides and polysaccharides. As used herein, the term "monosaccharides" refers to hydroxy aldehydes or hydroxy ketones that cannot be hydrolyzed to smaller units. Examples of monosaccharides include, but are not limited to, dextrose, glucose, fructose and galactose. As used herein, the term "polysaccharides" refers to saccharides comprising two or more monosaccharide units. Examples of polysaccharides include, but are not limited to, sucrose, maltose, cellobiose, cellulose and lactose.

Prior to treatment with the digestive solvent, the untreated biomass can be washed and/or reduced in size (e.g., chopping, crushing or debarking) to a convenient size and certain quality that aids in moving the biomass or mixing and impregnating the chemicals from digestive solvent. Thus, in some embodiments, providing biomass can comprise harvesting a lignocelluloses-containing plant such as, for example, a hardwood or softwood tree. The tree can be subjected to debarking, chopping to wood chips of desirable thickness, and washing to remove any residual soil, dirt and the like.

In the digestion system, the size-reduced biomass is contacted with the digestive solvent in at least one digester where the digestion reaction takes place. The digestive solvent must be effective to digest lignins.

In one aspect of the embodiment, the digestive solvent maybe a Kraft-like digestive solvent that contains (i) at least 0.5 wt %, preferably at least 4 wt %, to at most 20 wt %, more preferably to 10 wt %, based on the digestive solvent, of at least one alkali selected from the group consisting of sodium hydroxide, sodium carbonate, sodium sulfide, potassium hydroxide, potassium carbonate, ammonium hydroxide, and mixtures thereof, (ii) optionally, 0 to 3%, based on the digestive solvent, of anthraquinone, sodium borate and/or polysulfides; and (iii) water (as remainder of the digestive solvent). In some embodiments, the digestive solvent may have an active alkali of between 5 to 25%, more preferably between 10 to 20%. The term "active alkali"(AA), as used herein, is a percentage of alkali compounds combined, expressed as sodium oxide based on weight of the biomass less water content (dry solid biomass). If sodium sulfide is present in the digestive solvent, the sulfidity can range from about 15% to about 40%, preferably from about 20 to about 30%. The term "sulfidity", as used herein, is a percentage ratio of $Na_2S$, expressed as $Na_2O$, to active alkali. Digestive solvent to biomass ratio can be within the range of 0.5 to 50, preferably 2 to 10. The digestion is carried out typically at a cooking-liquor to biomass ratio in the range of 2 to 6, preferably 3 to 5. The digestion reaction is carried out at a temperature within the range of from about 60° C., preferably 100° C., to about 230° C., and a residence time within 0.25 h to 24 h. The reaction is carried out under conditions effective to provide a pretreated bio-based feedstock stream, and a chemical liquor stream containing alkali compounds and dissolved lignin and hemicelluloses material.

The digester can be, for example, a pressure vessel of carbon steel or stainless steel or similar alloy. The digestion system can be carried out in the same vessel or in a separate vessel. The cooking can be done in continuous or batch mode. Suitable pressure vessels include, but are not limited to the "PANDIA™ Digester" (Voest-Alpine Industrienlagenbau GmbH, Linz, Austria), the "DEFIBRATOR Digester" (Sunds Defibrator AB Corporation, Stockholm, Sweden), M&D (Messing & Durkee) digester (Bauer Brothers Company, Springfield, Ohio, USA) and the KAMYR Digester (Andritz Inc., Glens Falls, N.Y., USA). The digestive solvent has a pH from 10 to 14, preferably around 12 to 13 depending on the concentration of active alkali AA. The contents can be kept at a temperature within the range of from 100° C. to 230° C. for a period of time, more preferably within the range from about 130° C. to about 180° C. The period of time can be from about 0.25 to 24.0 hours, preferably from about 0.5 to about 2 hours, after which the pretreated contents of the digester are discharged. For adequate penetration, a sufficient volume of liquor is required to ensure that all the biomass surfaces are wetted. Sufficient liquor is supplied to provide the specified digestive solvent to biomass ratio. The effect of greater dilution is to decrease the concentration of active chemical and thereby reduce the reaction rate.

In a system using the digestive solvent such as a Kraft-like digestive solvent similar to those used in a Kraft pulp and paper process, the chemical liquor may be regenerated in a similar manger to a Kraft pulp and paper chemical regeneration process. For example, in reference to FIG. 3 when used in a Kraft-like digestive solvent system, the recaustisized chemical recycle stream obtained by regenerating at least a portion of the solvent liquor stream through a chemical regeneration system. In an embodiment, chemical liquor stream is obtained by concentrating at least a portion of the solvent liquor stream in a concentration system thereby producing a concentrated chemical liquor stream then burning the concentrated chemical liquor stream in a boiler system thereby producing chemical recycle stream and a flue gas stream then converting the sodium containing compounds to sodium hydroxide in the recaustisizing system by contacting with lime (CaO) producing the recaustisized chemical recycle stream that can be used as a portion of the digestive solvent containing sodium hydroxide.

In another embodiment, an at least partially water miscible organic solvent that has partial solubility in water, preferably greater than 2 weight percent in water, may be used as digestive solvent to aid in digestion of lignin, and the nitrogen, and sulfur compounds. In one such embodiment, the digestive solvent is a water-organic solvent mixture with optional inorganic acid promoters such as HCl or sulfuric acid. Organic solvents exhibiting full or partial water solubility are preferred digestive solvents. In such a process, the organic digestive solvent mixture can be, for example, methanol, ethanol, acetone, ethylene glycol, triethylene glycol and tetrahydrofurfuryl alcohol. Organic acids such as acetic, oxalic, acetylsalicylic and salicylic acids can also be used as catalysts (as acid promoter) in the at least partially miscible organic solvent process. Temperatures for the digestion may range from about 130 to about 220 degrees Celsius, preferably from about 140 to 180 degrees Celsius, and contact times from 0.25 to 24 hours, preferably from about one to 4 hours. Preferably, a pressure from about 1 to 80 bar, and most typically from about 5 to 50 bar, is maintained on the system to avoid boiling or flashing away of the solvent.

Optionally the pretreated biomass stream can be washed prior to hydrogenolysis. In the wash system, the pretreated biomass stream can be washed to remove one or more of non-cellulosic material, and non-fibrous cellulosic material prior to hydrogenolysis. The pretreated biomass stream is optionally washed with a water stream under conditions to remove at least a portion of lignin, hemicellulosic material, and salts in the pretreated biomass stream. For example, the pretreated biomass stream can be washed with water to remove dissolved substances, including degraded, but non-processable cellulose compounds, solubilised lignin, and/or any remaining alkaline chemicals such as sodium compounds that were used for cooking or produced during the cooking (or pretreatment). The washed pretreated biomass stream may contain higher solids content by further processing such as mechanical dewatering as described below.

In a preferred embodiment, the pretreated biomass stream is washed counter-currently. The wash can be at least partially carried out within the digester and/or externally with separate washers. In one embodiment of the invention process, the wash system contains more than one wash steps, for example, first washing, second washing, third washing, etc. that produces washed pretreated biomass stream from first washing, washed pretreated biomass stream from second washing, etc. operated in a counter current flow with the water, that is then sent to subsequent processes as washed pretreated biomass stream. The water is recycled through first recycled wash stream and second recycled wash stream and then to third recycled wash stream. Water recovered from the chemical liquor stream by the concentration system can be recycled as wash water to wash system. It can be appreciated that the washed steps can be conducted with any number of steps to obtain the desired washed pretreated biomass stream. Additionally, the washing may adjust the pH for subsequent steps where the pH is about 2.0 to 10.0, where optimal pH is determined by the catalyst employed in the hydrogenolysis step. Bases such as alkali base may be optionally added, to adjust pH.

In the embodiment shown in FIG. 2 and FIG. 3, the bio-based feedstocks are optionally reacted in a hydrogenation reaction and then a hydrogenolysis reaction to form suitable stable hydroxyl intermediates that comprise glycols for further processing. In an embodiment of the invention, the hydrogenation reaction is optional and the hydrogenolysis reaction alone is suitable to form the desired glycols. In another embodiment of the invention, the carbohydrates are passed through the hydrogenolysis reaction prior to being passed through the hydrogenation reaction (thus hydrogenolysis reaction and hydrogenation reaction are reversed from the order). In an embodiment of the invention, the hydrogenation and hydrogenolysis reactions occur in the same vessel to generate glycols and other stable oxygenated intermediates to be fed into a processing reaction and separation. In an embodiment, water removal could be conducted prior to the hydrogenolysis reaction.

In one embodiment of the invention, the bio-based feedstock is optionally first hydrolyzed in a liquid medium such as an aqueous solution or aqueous solution with organic solvent (e.g., a recycled portion of the monooxygenates), to obtain an aqueous carbohydrate stream for use in the process. Various biomass hydrolysis methods may be suitable, including, but not limited to, acid hydrolysis, alkaline hydrolysis, enzymatic hydrolysis, and hydrolysis using hot-compressed water. In certain embodiments, the hydrolysis reaction can occur at a temperature between 100° C. and 250° C. and pressure between about 100 kPa and 10,000 kPa. In embodiments including strong acid and enzymatic hydrolysis, the hydrolysis reaction can occur at temperatures as low as ambient temperature and pressure between 100 kPa and 10,000 kPa. In some embodiments, the hydrolysis reaction may comprise a hydrolysis catalyst (e.g., a metal or acid catalyst) to aid in the hydrolysis reaction. The hydrolysis catalyst can be any catalyst capable of effecting a hydrolysis reaction. For example, suitable hydrolysis catalysts include, but are not limited to, acid catalysts, base catalysts, metal catalysts, and any combination thereof. Acid catalysts can include organic acids such as acetic acid, formic acid, and levulinic acid. Base catalysts can include caustics. In an embodiment, the acid catalyst can be generated as a byproduct during the hydrogenation and/or hydrogenolysis reactions. In certain embodiments, the hydrolysis of the bio-based feedstocks can occur in conjunction with the hydrogenation and/or hydrogenolysis reactions. In such embodiments, a co-catalyst or catalytic support may be added to the hydrogenation and/or hydrogenolysis reactions to facilitate the hydrolysis reaction.

Various factors affect the conversion of the bio-based feedstock in the hydrolysis reaction. In some embodiments, hemicellulose can be extracted from the bio-based feedstock within an aqueous fluid and hydrolyzed at temperatures below 160° C. to produce a C5 carbohydrate fraction. At increasing temperatures, this C5 fraction can be thermally degraded. It is therefore advantageous to convert the C5, C6, or other sugar intermediates directly into more stable intermediates such as sugar alcohols (monooxygenates). By recycling a portion of the monooxygenates from the hydrogenation and/or hydrogenolysis reactions and performing additional biomass hydrolysis with this recycled liquid, the concentration of active stable hydroxyl intermediates can be increased to commercially viable concentrations without water dilution. Typically, a concentration of at least 2%, or 5% or preferable greater than 8% of total organic intermediates (e.g., the recycled stable hydroxyl intermediates plus the hydrolyzed carbohydrates) in water, may be suitable for a viable process. This may be determined by sampling the intermediate stream at the outlet of the hydrolysis reaction and using a suitable technique such as chromatography to identify the concentration of total organics.

Cellulose extraction begins above 160° C., with solubilization and hydrolysis becoming complete at temperatures around 190° C., aided by organic acids (e.g., carboxylic acids) formed from partial degradation of carbohydrate components. Some lignins can be solubilized before cellulose, while other lignins may persist to higher temperatures. Organic in situ generated solvents, which may comprise a portion of the monooxygenates, including, but not limited to, light alcohols and glycols, can assist in solubilization and extraction of lignin and other components.

At temperatures ranging from 250° C. to 275° C., carbohydrates can degrade through a series of complex self-condensation reactions to form caramelans, which are considered degradation products that are difficult to convert to fuel products. In general, some degradation reactions can be expected with aqueous reaction conditions upon application of temperature, given that water will not completely suppress oligomerization and polymerization reactions.

The temperature of the hydrolysis reaction can be chosen so that the maximum amount of extractable carbohydrates are hydrolyzed and extracted as carbohydrates from the bio-based feedstock while limiting the formation of degradation products. In some embodiments, a plurality of reactor vessels may be used to carry out the hydrolysis reaction. These vessels may have any design capable of carrying out a hydrolysis reaction. Suitable reactor vessel designs can include, but are not limited to, co-current, counter-current, stirred tank, and/or fluidized bed reactors. In this embodiment, the bio-based feedstock may first be introduced into a reactor vessel operating at approximately 160° C. At this temperature the hemicellulose may be hydrolyzed to extract the C5 carbohydrates and some lignin without degrading these products. The remaining bio-based feedstock solids may then exit the first reactor vessel and pass to a second reactor vessel. The second vessel may be operated between 160° C. and 250° C. so that the cellulose is further hydrolyzed to form C6 carbohydrates. The remaining bio-based feedstock solids may then exit the second reactor as a waste stream while the intermediate stream from the second reactor can be cooled and combined with the intermediate stream from the first reactor vessel. The combined outlet stream may then pass to the hydrogenation and/or hydrogenolysis reactors. In another embodiment, a series of reactor vessels may be used with an increasing temperature profile so that a desired carbohydrate fraction is extracted in each vessel. The outlet of each vessel can then be cooled prior to combining the streams, or the streams can be individually fed to the hydrogenation/and or hydrogenolysis reaction for conversion of the intermediate carbohydrate streams to one or more stable hydroxyl intermediate streams.

In another embodiment, the hydrolysis reaction may take place in a single vessel. This vessel may have any design capable of carrying out a hydrolysis reaction. Suitable reactor vessel designs can include, but are not limited to, co-current, counter-current, stirred tank, or fluidized bed reactors. In some embodiments, a counter-current reactor design is used in which the bio-based feedstock flows counter-current to the aqueous stream, which may comprise an in situ generated solvent. In this embodiment, a temperature profile may exist within the reactor vessel so that the temperature within the hydrolysis reaction media at or near the bio-based feedstock inlet is approximately 160° C. and the temperature near the bio-based feedstock outlet is approximately 200° C. to 250° C. The temperature profile may be obtained through the introduction of an aqueous fluid comprising an in situ generated solvent above 200° C. to 250° C. near the bio-based feedstock outlet while simultaneously introducing a bio-based feedstock at 160° C. or below. The specific inlet temperature of the aqueous fluid and the bio-based feedstock will be determined based on a heat balance between the two streams. The resulting temperature profile may be useful for the hydrolysis and extraction of cellulose, lignin, and hemicellulose without the substantial production of degradation products.

In one embodiment, the conversion of carbohydrate or sugar alcohol in the first reaction zone is limited to less than 80%, preferably less than 70%, more preferably less than 60%, most preferably less than 50%, to maximize selectivities to glycols. In another embodiment, the conversion of carbohydrates and sugar alcohols to monooxygenated compounds across the first reaction system or zone and second reaction system or zone is less than 90%.

Other means may be used to establish an appropriate temperature profile for the hydrolysis reaction and extraction of cellulose and hemicellulose along with other components such as lignin without substantially producing degradation products. For example, internal heat exchange structures may be used within one or more reaction vessels to maintain a desired temperature profile for the hydrolysis reaction. Other structures as would be known to one of ordinary skill in the art may also be used.

In certain embodiments, the hydrolysis reaction, hydrogenation reaction, hydrogenolysis reaction, and processing reactions described in the present invention could be conducted in a single step.

Each reactor vessel of the invention preferably includes an inlet and an outlet adapted to remove the product stream from the vessel or reactor. In some embodiments, the vessel in which hydrolysis reaction or some portion of the hydrolysis reaction occurs may include additional outlets to allow for the removal of portions of the reactant stream to help maximize the desired product formation. A backmixed reactor (e.g., a stirred tank, a bubble column, and/or a jet mixed reactor) may be employed if the viscosity and characteristics of the partially digested bio-based feedstock and liquid reaction media is sufficient to operate in a regime where bio-based feedstock solids are suspended in an excess liquid phase (as opposed to a stacked pile digester).

Further, yields of glycols and liquid fuels and energy efficiency are improved by staging the reaction temperatures from a lower temperature (in the range of 120 to about 230° C., most preferably in the range of 180 and 215° C. in the first reaction system or zone, where carbohydrate feed is converted to hydrogenolysis intermediate, followed by a second reaction system or zone operated in the range of 220 to 250° C. where the monooxygenates-rich stream is produced. Complex carbohydrate feed components must first be hydrolyzed with water to form monomeric sugars containing carbonyl or aldehydic functionality. These reactive groups are readily hydrogenated at a low temperature (above about 100° C.), to stabilize against self condensation to form caramelan or heavy ends tars. Use of lower temperature for the first reaction system or zone, minimizes heavy ends formation relative to hydrogenation, and hydrogenolysis to form the desired glycol intermediates.

We have discovered that the further reaction of glycols and polyols to form monooxygenates occurs at a slower rate average, and is advantaged via use of a higher temperature for the second reaction system or zone. The hydrogenation and hydrogenolysis reaction are exothermic, such that addition of process heat from external sources is not required, to obtain an increase in the steady state average temperature from the first reaction system or zone, to the second reaction system or zone. Use of higher average steady state temperatures in the second reaction zone also insures complete hydrogenation of carbohydrates and derivatives containing more than two oxygen atoms per molecule, as such that the monooxygenates-rich stream processed to liquid fuels has a higher effective hydrogen-to-carbon ratio, defined (G. W. Huber et al. Energy Environ. Sci., 2011, 4, 2297) as $(H/C)_{eff} = (H-2O)/C$. Higher $(H/C)_{eff}$ provides reduced coking for acidic catalysts used to convert the monooxygenates-rich stream to liquid hydrocarbon fuels. Use of too high a temperature in the second reaction system or zone, leads to formation of alkanes from monooxygenates. While $C_5+$ alkanes can be incorporated directly into liquid fuels, there is a desire not to convert $C_4-$ monooxygenates into the corresponding alkanes, as the monooxygenates can be dimerized or trimerized to a desirable fuel component in the fuel conversion step, whereas alkanes are nonreactive, such that $C_4-$ fraction is lost as byproduct gas.

It is therefore advantageous to operate the second reaction system or zone at a higher maximum or average steady state reaction temperature than the first reaction system or zone, to minimize heavy ends formation, maximize yields of glycols and liquid fuels, with minimal deactivation of catalysts due to coke deposition, and minimization of the amount of process energy required to be added from external sources.

It is understood that in one embodiment, the biomass does not need to be hydrolyzed, as the carbohydrate containing biomass may already be in suitable aqueous form (e.g., raw cane juice concentrate) for converting the bio-based feedstock to higher hydrocarbons.

In an embodiment of the invention, the intermediate carbohydrate stream produced by the hydrolysis reaction may be converted to stable hydroxyl intermediates including, but not limited to, glycols, and alcohols. In general, without being limited by any particular theory, a suitable conversion reaction or reactions can include, without limitation: hydrogenolysis, consecutive hydrogenation-hydrogenolysis, consecutive hydrogenolysis-hydrogenation, and combined hydrogenation-hydrogenolysis reactions, resulting in the formation of monooxygenates that can be easily converted to higher hydrocarbons by one or more processing reactions.

In an embodiment of the invention, it is desirable to convert the carbohydrates and optionally a portion of monooxygenates to smaller molecules that will be more readily converted to desired higher hydrocarbons. A suitable method for this conversion is through a hydrogenolysis reaction.

Various processes are known for performing hydrogenolysis of carbohydrates. One suitable method includes contacting a carbohydrate or monooxygenates with hydrogen or hydrogen mixed with a suitable gas and a hydrogenolysis catalyst in a hydrogenolysis reaction under conditions sufficient to form a reaction product comprising smaller molecules or glycols. Most typically, hydrogen is dissolved in the liquid mixture of carbohydrate, which is in contact with the catalyst under conditions to provide catalytic reaction. At least a portion of the carbohydrate feed is contacted directly with hydrogen in the presence of the hydrogenolysis catalyst. By the term "directly", the reaction is carried out on at least a portion of the carbohydrate without necessary stepwise first converting all of the carbohydrates into a stable hydroxyl intermediate. As used herein, the term "smaller molecules or glycols" includes any molecule that has a lower molecular weight, which can include a smaller number of carbon atoms or oxygen atoms than the starting carbohydrate. In an embodiment, the reaction products include smaller molecules that include glycols and alcohols.

In an embodiment, a carbohydrate (e.g., a 5 and/or 6 carbon carbohydrate molecule) can be converted to monooxygenates as hydrogenolysis stream comprising propylene glycol, ethylene glycol, and glycerol using a hydrogenolysis reaction in the presence of a hydrogenolysis catalyst. The hydrogenolysis catalyst may include Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. The promoters may allow for hydrogenation and hydrogenolysis reactions to occur at the same time. The hydrogenolysis catalyst can also include a carbonaceous pyropolymer catalyst containing transition metals (e.g., chromium, molybdemum, tungsten, rhenium, manganese, copper, cadmium) or Group VIII metals (e.g., iron, cobalt, nickel, platinum, palladium, rhodium, ruthenium, iridium, and osmium). In certain embodiments, the hydrogenolysis catalyst can include any of the above metals combined with an alkaline earth metal oxide or adhered to a catalytically active support. In certain embodiments, the catalyst described in the hydrogenolysis reaction can include a catalyst support as described herein for the hydrogenation reaction. Further, a supported hydrogenolysis catalyst containing (a) sulfur and (b) molybdenum and/or tungsten and (c) cobalt and/or nickel may be used, particularly if a sulfur poison tolerant catalyst is preferred.

The conditions for which to carry out the hydrogenolysis reaction will vary based on the type of starting material and the desired products. One of ordinary skill in the art, with the benefit of this disclosure, will recognize the appropriate conditions to use to carry out the reaction. In general, the hydrogenolysis reaction is conducted at temperatures of at least 110° C., and preferably from at 150° C. to 240° C., and most preferably at 180° C. to 220° C. In an embodiment, the hydrogenolysis reaction is conducted under basic conditions, preferably at a pH of 8 to 13, and even more preferably at a pH of 10 to 12. In an embodiment, the hydrogenolysis reaction is conducted at 0.1 to 150 bar of hydrogen and pressures in a range between 60 kPa and 16500 kPa, and preferably in a range between 1700 kPa and 14000 kPa, and even more preferably between 4800 kPa and 11000 kPa.

The hydrogen used in the hydrogenolysis reaction of the current invention can include external hydrogen, recycled hydrogen, in situ generated hydrogen, and any combination thereof.

In an embodiment, the use of a hydrogenolysis reaction may produce less carbon dioxide and a greater amount of glycols than a reaction that results in reforming of the reactants. For example, reforming can be illustrated by formation of isopropanol (i.e., IPA, or 2-propanol) from sorbitol:

$$C_6H_{14}O_6 + H_2O \rightarrow 4H_2 + 3CO_2 + C_3H_8O; \; dHR = -40 \text{ J/gmol} \quad \text{(Eq. 1)}$$

Alternately, in the presence of hydrogen, glycols and mono-oxygenates such as IPA can be formed by hydrogenolysis, where hydrogen is consumed rather than produced:

$$C_6H_{14}O_6 + 3H_2 \rightarrow 2H_2O + 2C_3H_8O_2; \; dHR = +81 \text{ J/gmol} \quad \text{(Eq. 2)}$$

$$C_6H_{14}O_6 + 5H_2 \rightarrow 4H_2O + 2C_3H_8O; \; dHR = -339 \text{ J/gmol} \quad \text{(Eq. 3)}$$

As a result of the differences in the reaction conditions (e.g., temperatures below 250° C.), the products of the hydrogenolysis reaction may comprise greater than 5%%, preferably 10% by mole, or alternatively, greater than 20% by mole, of glycols, which may result in a greater conversion in a processing reaction. In addition, the use of a hydrolysis reaction rather than a reaction running at reforming conditions may result in less than 10% by mole, or alternatively less than 20% by mole carbon dioxide production.

In an embodiment, hydrogenolysis is conducted under neutral or acidic conditions, as needed to accelerate hydrolysis reactions in addition to the hydrogenolysis.

In an embodiment of the invention, a hydrolyzed, substantially hydrolyzed, or non-hydrolyzed biomass-derived carbohydrate may converted into glycols and other monooxygenates comprising the corresponding alcohol derivative through a hydrogenolysis reaction in addition to an optional hydrogenation reaction in a suitable hydrogenation reaction vessel.

The carbohydrates, glycols and other monooxygenates, from the hydrolysis reaction, or both may take place in a hydrogenation reaction to saturate one or more unsaturated bonds. Various processes are suitable for hydrogenating carbohydrates, glycols and other monooxygenates or both. One method includes contacting a feed stream with hydrogen or hydrogen mixed with a suitable gas and a catalyst under conditions sufficient to cause a hydrogenation reaction to form a hydrogenated product. The hydrogenation catalyst generally can include a Group VIII metal and/or a Group VI metal. Examples of such a catalyst can include, but is not limited to, Cu, Re, Ni, Fe, Co, Ru, Pd, Rh, Pt, Os, Ir, and alloys or any combination thereof, either alone or with promoters such as W, Mo, Au, Ag, Cr, Zn, Mn, Sn, B, P, Bi, and alloys or any combination thereof. Other effective hydrogenation catalyst materials include either supported nickel or ruthenium modified with rhenium. In an embodiment, the hydrogenation catalyst also includes any one of the supports described below, depending on the desired functionality of the catalyst. The hydrogenation catalysts may be prepared by methods known to those of ordinary skill in the art.

In an embodiment, the hydrogenation catalyst includes a supported Group VIII metal catalyst and a metal sponge material (e.g., a sponge nickel catalyst). Raney nickel provides an example of an activated sponge nickel catalyst suitable for use in this invention. In an embodiment, the hydrogenation reaction in the invention is performed using a catalyst comprising a nickel-rhenium catalyst or a tungsten-modified nickel catalyst. One example of a suitable catalyst for the hydrogenation reaction of the invention is a carbon-supported nickel-rhenium catalyst.

In an embodiment, a suitable Raney nickel catalyst may be prepared by treating an alloy of approximately equal amounts by weight of nickel and aluminum with an aqueous alkali solution, e.g., containing about 25 weight % of sodium hydroxide. The aluminum is selectively dissolved by the aqueous alkali solution resulting in a sponge shaped material comprising mostly nickel with minor amounts of aluminum. The initial alloy includes promoter metals (e.g., molybdenum or chromium) in the amount such that 1 to 2 weight % remains in the formed sponge nickel catalyst. In another embodiment, the hydrogenation catalyst is prepared using a solution of ruthenium(III) nitrosylnitrate, ruthenium (III) chloride in water to impregnate a suitable support material. The solution is then dried to form a solid having a water content of less than 1% by weight. The solid is then reduced at atmospheric pressure in a hydrogen stream at 300° C. (uncalcined) or 400° C. (calcined) in a rotary ball furnace for 4 hours. After cooling and rendering the catalyst inert with nitrogen, 5% by volume of oxygen in nitrogen is passed over the catalyst for 2 hours.

In certain embodiments, the catalyst described includes a catalyst support. The catalyst support stabilizes and supports the catalyst. The type of catalyst support used depends on the chosen catalyst and the reaction conditions. Suitable supports for the invention include, but are not limited to, carbon, silica, silica-alumina, zirconia, titania, ceria, vanadia, nitride, boron nitride, heteropolyacids, hydroxyapatite, zinc oxide, chromia, zeolites, carbon nanotubes, carbon fullerene and any combination thereof.

The catalysts used in this invention can be prepared using conventional methods known to those in the art. Suitable methods may include, but are not limited to, incipient wetting, evaporative impregnation, chemical vapor deposition, wash-coating, magnetron sputtering techniques, and the like.

The conditions for which to carry out the hydrogenation reaction will vary based on the type of starting material and the desired products. One of ordinary skill in the art, with the benefit of this disclosure, will recognize the appropriate reaction conditions. In general, the hydrogenation reaction is conducted at temperatures of 40° C. to 250° C., and preferably at 90° C. to 200° C., and most preferably at 100° C. to 150° C. In an embodiment, the hydrogenation reaction is conducted at pressures from 500 kPa to 14,000 kPa.

In some embodiments, a plurality of reactor vessels may be used to carry out the hydrogenation reaction. The plurality of vessels may be capable of carrying out a hydrogenation reaction without producing unwanted byproducts while minimizing degradation of wanted products. In an embodiment, the hydrogenation reaction may occur in two or more stages. In this embodiment, the bio-based feedstock may first be introduced into a first stage reaction operating at a temperature between 40° C. to 90° C. The products may then be exposed to a second stage reaction operating at a temperature between 80° C. to 120° C. The remaining products may then be exposed to a third stage operating at a temperature between 120° C. and 190° C. In an embodiment, the hydrogen used in the hydrogenation reaction of the current invention can include external hydrogen, recycled hydrogen, in situ generated hydrogen, and any combination thereof. As used herein, the term "external hydrogen" refers to hydrogen that does not originate from the bio-based feedstock reaction itself, but rather is added to the system from another source.

In an embodiment, the invention comprises a system having a first reactor for receiving a carbohydrate and producing a hydrogenated product. Each reactor of the invention preferably includes an inlet and an outlet adapted to remove the product stream from the reactor. In an embodiment, the reactors include additional outlets to allow for the removal of portions of the reactant stream to help maximize the desired product formation, and allow for collection and recycling of by-products for use in other portions of the system.

In an embodiment, the invention comprises a system having a second reactor system for receiving the hydrogenated product and converting it into an alcohol and a polyol through a hydrolysis reaction. In certain embodiments, the hydrogenation and hydrogenolysis catalysts are the same and may exist in the same bed in the same vessel. Each reactor of the invention preferably includes an inlet and an outlet adapted to remove the product stream from the reactor. In an embodiment, the reactor may include additional outlets to allow for the removal of portions of the reactant stream to help maximize the desired product formation, and allow for collection and recycling of by-products for use in other portions of the system.

In an embodiment, the system of the invention includes elements that allow for the separation of the hydrogenolysis stream into different components to promote the desired products being fed into the second reaction system and the first separation system. For example, a suitable separator unit includes, but is not limited to, a phase separator, stripping column, extractor, or distillation column.

In some embodiments, an outlet stream comprising at least a portion of the hydrogenolysis stream can pass to a processing reaction that may comprise a condensation reaction. In an embodiment, the oxygen to carbon ratio of the higher hydrocarbons produced through the condensation reaction is less than 0.5, alternatively less than 0.4, or preferably less than 0.3 Formation of ethylene glycol and 1,2-propylene glycol occurs during the aqueous phase reforming reaction of sugars and carbohydrates. Continued reaction of these intermediates results in the formation of ethanol, 1-propanol and 2-propanol, which can be condensed or dehydrated and oliogomerized to higher molecular weight components suitable for liquid biofuels, in a subsequent reaction step. Relative rates of reaction for the various conversion steps results in an observable concentration of ethylene glycol and propylene glycol in the intermediate reaction mixture, under appropriate conditions.

Mono-oxygenate reaction intermediates are preferred for subsequent condensation and oligomerization steps, and are more volatile than ethylene glycol and propylene glycol, which themselves are more volatile than sugars such as glucose, xylose, mannose, or complex sugars such as sucrose, and than the corresponding sugar alcohols such as sorbitol. Mono-oxygenates and at least a fraction of water present in the reaction mixture may therefore be separated as an overheaded product via flash or multistage distillation. Continued distillation will separate remaining water with ethylene and propylene glycol, as a second product. Unconverted sugars and sugar alcohols, and byproduct glycerol will be concentrated in the bottoms product from the distillation.

A single distillation column may be employed, with separation of ethylene glycol, propylene glycol and some water as a side draw stream, with removal of monooxygenates and some water as a tops stream, and sugar and sugar alcohol with some glycerol as a bottoms stream. Alternately, two distillation columns or flashers may be employed in series, with production of monoxygenates and water as the overhead product from the first flasher or distillation column, and production of ethylene glycol and propylene glycol as the overhead product of a second distillation column, with sugars, unconverted sugar alcohols, and other heavy ends as a bottoms product. The ethylene glycol and propylene glycol streams may optionally be sent to a distillation column for separation into individual components.

Light gases such as $CO_2$, $H_2$, and alkanes may be removed first by flashing, or be removed as an overhead vapor stream from the first flasher or distillation column Flashers may entail an open vessel or a packed or trayed vessel. Distillation columns may be packed, or trayed, or employ a catalyst for further conversion of intermediates present.

A portion of the hydrogenolysis stream provided to a second reaction system containing a hydrogenolysis catalyst at a temperature in the range of 160 to 280° C., preferably 210 to 260° C. and in the presence of 0.1 to 150 bar hydrogen to produce a oxygenated intermediate stream comprising of 5 wt % of monooxygenated hydrocarbons of chain length less than 6 carbons, based on the total. In an embodiment, the second reaction system is conducted under basic conditions, preferably at a pH of 8 to 13, and even more preferably at a pH of 10 to 12. In an embodiment, the hydrogenolysis reaction is conducted at pressures in a range between 60 kPa and 16500 kPa, and preferably in a range between 1700 kPa and 14000 kPa, and even more preferably between 4800 kPa and 11000 kPa.

It is generally preferred to operate the second reaction system or zone at a higher temperature than the first, to facilitate conversion of polyoxygenates to monooxygenate components. Temperature must however be limited to prevent full hydrogenation or hydrodeoxygenation of monooxygenates containing less than four carbons to alkanes, to minmimize the amount of light gas byproduct. Once fully hydrogenated to alkanes, it is not possible to increase chain length in subsequent condensation-oligomerization steps, and hence any alkane less than $C_5$ becomes a yield loss to light gas byproduct.

Optionally, a different catalyst may be used in the second reaction zone relative to the first reaction zone. Purification such as ion exchange or adsorption may be used prior to the first reaction zone or the second reaction zone, or both, to protect catalyst from impurities in the feed, or released during the hydrolysis of bio-based feeds during processing. Removal of protein derivatives such as amino acids containing N and sometimes S functional groups, may be required to prevent excessive rates of catalyst poisoning. Alternately, a poison-tolerant catalyst me be deployed in either of the reaction zones.

The hydrogen used in the hydrogenolysis reaction of the current invention can include external hydrogen, recycled hydrogen, in situ generated hydrogen, and any combination thereof.

The conditions for which to carry out the hydrogenolysis reaction will vary based on the type of starting material and the desired products after further process to form the liquid fuel.

At least a portion of said hydrogenolysis stream is provided to the first separation system such as a light ends column, that removes a small portion of monooxygenates formed in the hydrogenolysis system with water by flashing to provide a glycol enriched stream 210 and monooxygenates-rich stream 208 also containing other organics. The glycol enriched stream as a second portion (bottoms) from the first separation system is provided to a second separation system 220, a polyols recovery column, where EG and PG are separated overhead as glycol stream 224 and heavier stream containing heavier glyols and unconverted carbohydrates (sorbitol) are optionally recycled back to the feed 102 or hydrogenolysis system 106. The monooxygenates-rich stream generally contains monooxygenates, as well as some polyoxygenated compounds, alkanes, and water, and the glycol rich contains at least 10 wt %, preferably 15 wt %, more preferably 20 wt %, most preferably 25 wt %, based on the total oxygenates content, of glycols. The glycols can be recovered from the glycol rich stream by conventional recovery methods such as, for example, distillation or can be used as solvents or feedstocks for other processes. The flashing may be carried out at a temperature in the range of about 150 to 280° C. and pressure in the range of 0.5 to 5 bar absolute.

A portion of the oxygenated intermediates can be processed to produce a fuel blend in one or more processing reactions. In an embodiment, a condensation reaction can be used along with other reactions to generate a fuel blend and may be catalyzed by a catalyst comprising acid or basic functional sites, or both. In general, without being limited to any particular theory, it is believed that the basic condensation reactions generally consist of a series of steps involving: (1) an optional dehydrogenation reaction; (2) an optional dehydration reaction that may be acid catalyzed; (3) an aldol condensation reaction; (4) an optional ketonization reaction; (5) an optional furanic ring opening reaction; (6) hydrogenation of the resulting condensation products to form a C4+ hydrocarbon; and (7) any combination thereof. Acid catalyzed condensations may similarly entail optional hydrogenation or dehydrogenation reactions, dehydration, and oligomerization reactions. Additional polishing reactions may also be used to conform the product to a specific fuel standard, including reactions conducted in the presence of hydrogen and a hydrogenation catalyst to remove functional groups from final fuel product. A catalyst comprising a basic functional site, both an acid and a basic functional site, and optionally comprising a metal function, may be used to effect the condensation reaction.

"Acidic" conditions or "acidic functionality" for the catalysts refer to either Bronsted or Lewis acid acidity. For Bronsted acidity, the catalyst is capable of donating protons (designed as $H^+$) to perform the catalytic reaction, under the conditions present in the catalytic reactor. Acidic ion exchange resins, phosphoric acid present as a liquid phase on a support, are two examples. Metal oxides such as silica, silica-aluminas, promoted zirconia or titania can provide protons $H^+$ associated with Bronsted acidiy in the presence of water or water vapor. Lewis acidity entails ability to accept an electron pair, and most typically is obtained via the presence of metal cations in a mixed metal-oxide framework such as silica-alumina or zeolite. Determination of acidic properties can be done via adsorption of a base such as ammonia, use of indictors, or via use of a probe reaction such as dehydration of an alcohol to an olefin, which is acid catalyzed. "Basic" conditions or "base functionality" for the catalysts can refer to either Bronsted or Lewis basicity. For Bronsted basicity, hydroxide anion is supplied by the catalyst, which may be present as an ion exchange resin, or supported liquid phase catalyst, mixed metal oxide with promoter such as alkali, calcium, or magnesium, or in free solution. Lewis base catalysis refers to the conditions where Lewis base catalysis is the process by which an electron pair donor increases the rate of a given chemical reaction by interacting with an acceptor atom in one of the reagents or substrate (see Scott E. Denmark and Gregory L. Beutner, Lewis Base Catalysis in Organic Synthesis, Angew. Chem. Int. Ed. 2008, 47, 1560-1638). Presence and characterization of basic sites for a heterogeneous catalyst may be determined via sorption of an acidic component, use of probe reactions, or use of indicators. (see K. Tanabe, M. Misono, Y. Ono, H. Hattori (Eds.), New Solid Acids and Bases, Kodansha/Elsevier, Tokyo/Amsterdam, 1989, pp. 260-267). Catalysts such as mixed metal oxides may be "amphoteric", or capable of acting as acidic or basic catalysts depending on process conditions (pH, water concentration), or exhibit both acidic and basic properties under specific operating conditions, as a result of surface structures generated during formulation, or in situ during use to effect catalytic reactions In an embodiment, the aldol condensation reaction may be used to produce a fuel blend meeting the requirements for a diesel fuel or jet fuel. Traditional diesel fuels are petroleum distillates rich in paraffinic hydrocarbons. They have boiling ranges as broad as 187° C. to 417° C., which are suitable for combustion in a compression ignition engine, such as a diesel engine vehicle. The American Society of Testing and Materials (ASTM) establishes the grade of diesel according to the boiling range, along with allowable ranges of other fuel properties, such as cetane number, cloud point, flash point, viscosity, aniline point, sulfur content, water content, ash content, copper strip corrosion, and carbon residue. Thus, any fuel blend meeting ASTM D975 can be defined as diesel fuel.

The present invention also provides methods to produce jet fuel. Jet fuel is clear to straw colored. The most common fuel is an unleaded/paraffin oil-based fuel classified as Aeroplane A-1, which is produced to an internationally standardized set of specifications. Jet fuel is a mixture of a large number of different hydrocarbons, possibly as many as a thousand or more. The range of their sizes (molecular weights or carbon numbers) is restricted by the requirements for the product, for example, freezing point or smoke point. Kerosene-type Airplane fuel (including Jet A and Jet A-1) has a carbon number distribution between about C8 and C16. Wide-cut or naphtha-type Airplane fuel (including Jet B) typically has a carbon number distribution between about C5 and C15. A fuel blend meeting ASTM D1655 can be defined as jet fuel.

In certain embodiments, both Airplanes (Jet A and Jet B) contain a number of additives. Useful additives include, but are not limited to, antioxidants, antistatic agents, corrosion inhibitors, and fuel system icing inhibitor (FSII) agents. Antioxidants prevent gumming and usually, are based on alkylated phenols, for example, AO-30, AO-31, or AO-37. Antistatic agents dissipate static electricity and prevent sparking. Stadis 450 with dinonylnaphthylsulfonic acid (DINNSA) as the active ingredient, is an example. Corrosion inhibitors, e.g., DCI-4A are used for civilian and military fuels and DCI-6A is used for military fuels. FSII agents, include, e.g., Di-EGME.

In an embodiment, the oxygenated intermediates may comprise a carbonyl-containing compound that can take part in a base catalyzed condensation reaction. In some embodiments, an optional dehydrogenation reaction may be used to increase the amount of carbonyl-containing compounds in the oxygenated intermediate stream to be used as a feed to the condensation reaction. In these embodiments, the oxygenated intermediates and/or a portion of the bio-based feedstock stream can be dehydrogenated in the presence of a catalyst.

In an embodiment, a dehydrogenation catalyst may be preferred for an oxygenated intermediate stream comprising alcohols, diols, and triols. In general, alcohols cannot participate in aldol condensation directly. The hydroxyl group or groups present can be converted into carbonyls (e.g., aldehydes, ketones, etc.) in order to participate in an aldol condensation reaction. A dehydrogenation catalyst may be included to effect dehydrogenation of any alcohols, diols, or polyols present to form ketones and aldehydes. The dehydration catalyst is typically formed from the same metals as used for hydrogenation or aqueous phase reforming, which catalysts are described in more detail above. Dehydrogenation yields are enhanced by the removal or consumption of hydrogen as it forms during the reaction. The dehydrogenation step may be carried out as a separate reaction step before an aldol condensation reaction, or the dehydrogenation reaction may be carried out in concert with the aldol condensation reaction. For concerted dehydrogenation and aldol condensation, the dehydrogenation and aldol condensation functions can be on the same catalyst. For example, a metal hydrogenation/dehydrogenation functionality may be present on catalyst comprising a basic functionality.

The dehydrogenation reaction may result in the production of a carbonyl-containing compound. Suitable carbonyl-containing compounds include, but are not limited to, any compound comprising a carbonyl functional group that can form carbanion species or can react in a condensation reaction with a carbanion species, where "carbonyl" is defined as a carbon atom doubly-bonded to oxygen. In an embodiment, a carbonyl-containing compound can include, but is not limited to, ketones, aldehydes, furfurals, hydroxy carboxylic acids, and, carboxylic acids. The ketones may include, without limitation, hydroxyketones, cyclic ketones, diketones, acetone, propanone, 2-oxopropanal, butanone, butane-2,3-dione, 3-hydroxybutane-2-one, pentanone, cyclopentanone, pentane-2,3-dione, pentane-2,4-dione, hexanone, cyclohexanone, 2-methyl-cyclopentanone, heptanone, octanone, nonanone, decanone, undecanone, dodecanone, methylglyoxal, butanedione, pentanedione, diketohexane, dihydroxyacetone, and isomers thereof. The aldehydes may include, without limitation, hydroxyaldehydes, acetaldehyde, glyceraldehyde, propionaldehyde, butyraldehyde, pentanal, hexanal, heptanal, octanal, nonal, decanal, undecanal, dodecanal, and isomers thereof. The carboxylic acids may include, without limitation, formic acid, acetic acid, propionic acid, butanoic acid, pentanoic acid, hexanoic acid, heptanoic acid, isomers and derivatives thereof, including hydroxylated derivatives, such as 2-hydroxybutanoic acid and lactic acid. Furfurals include, without limitation, hydroxylmethylfurfural, 5-hydroxymethyl-2(5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl)ethanol, hydroxymethyltetrahydrofurfural, and isomers thereof. In an embodiment, the dehydrogenation reaction results in the production of a carbonyl-containing compound that is combined with the oxygenated intermediates to become a part of the oxygenated intermediates fed to the condensation reaction.

In an embodiment, an acid catalyst may be used to optionally dehydrate at least a portion of the oxygenated intermediate stream. Suitable acid catalysts for use in the dehydration reaction include, but are not limited to, mineral acids (e.g., HCl, $H_2SO_4$), solid acids (e.g., zeolites, ion-exchange resins) and acid salts (e.g., $LaCl_3$). Additional acid catalysts may include, without limitation, zeolites, carbides, nitrides, zirconia, alumina, silica, aluminosilicates, phosphates, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and any combination thereof. In some embodiments, the dehydration catalyst can also include a modifier. Suitable modifiers include La, Y, Sc, P, B, Bi, Li, Na, K, Rb, Cs, Mg, Ca, Sr, Ba, and any combination thereof. The modifiers may be useful, inter alia, to carry out a concerted hydrogenation/dehydrogenation reaction with the dehydration reaction. In some embodiments, the dehydration catalyst can also include a metal. Suitable metals include Cu, Ag, Au, Pt, Ni, Fe, Co, Ru, Zn, Cd, Ga, In, Rh, Pd, Ir, Re, Mn, Cr, Mo, W, Sn, Os, alloys, and any combination thereof. The dehydration catalyst may be self supporting, supported on an inert support or resin, or it may be dissolved in solution.

In some embodiments, the dehydration reaction occurs in the vapor phase. In other embodiments, the dehydration reaction occurs in the liquid phase. For liquid phase dehydration reactions, an aqueous solution may be used to carry out the reaction. In an embodiment, other solvents in addition to water, are used to form the aqueous solution. For example, water soluble organic solvents may be present. Suitable solvents can include, but are not limited to, hydroxymethylfurfural (HMF), dimethylsulfoxide (DMSO), 1-methyl-n-pyrollidone (NMP), and any combination thereof. Other suitable aprotic solvents may also be used alone or in combination with any of these solvents.

In an embodiment, the processing reactions may comprise an optional ketonization reaction. A ketonization reaction may increase the number of ketone functional groups within at least a portion of the oxygenated intermediate stream. For example, an alcohol or other hydroxyl functional group can be converted into a ketone in a ketonization reaction. Ketonization may be carried out in the presence of a base catalyst. Any of the base catalysts described above as the basic component of the aldol condensation reaction can be used to effect a ketonization reaction. Suitable reaction conditions are known to one of ordinary skill in the art and generally correspond to the reaction conditions listed above with respect to the aldol condensation reaction. The ketonization reaction may be carried out as a separate reaction step, or it may be carried out in concert with the aldol condensation reaction. The inclusion of a basic functional site on the aldol condensation catalyst may result in concerted ketonization and aldol condensation reactions.

In an embodiment, the processing reactions may comprise an optional furanic ring opening reaction. A furanic ring opening reaction may result in the conversion of at least a portion of any oxygenated intermediates comprising a furanic ring into compounds that are more reactive in an aldol condensation reaction. A furanic ring opening reaction may be carried out in the presence of an acidic catalyst. Any of the acid catalysts described above as the acid component of the aldol condensation reaction can be used to effect a furanic ring opening reaction. Suitable reaction conditions are known to one of ordinary skill in the art and generally correspond to the reaction conditions listed above with respect to the aldol condensation reaction. The furanic ring opening reaction may be carried out as a separate reaction step, or it may be carried out in concert with the aldol condensation reaction. The inclusion of an acid functional site on the aldol condensation catalyst may result in a concerted furanic ring opening reaction and aldol condensation reactions. Such an embodiment may be advantageous as any furanic rings can be opened in the presence of an acid functionality and reacted in an aldol condensation reaction using a base functionality. Such a concerted reaction scheme may allow for the production of a greater amount of higher hydrocarbons to be formed for a given oxygenated intermediate feed.

In an embodiment, production of a C4+ compound occurs by condensation, which may include aldol-condensation, of the oxygenated intermediates in the presence of a condensation catalyst. Aldol-condensation generally involves the carbon-carbon coupling between two compounds, at least one of which may contain a carbonyl group, to form a larger organic molecule. For example, acetone may react with hydroxymethylfurfural to form a C9 species, which may subsequently react with another hydroxymethylfurfural molecule to form a C15 species. The reaction is usually carried out in the presence of a condensation catalyst. The condensation reaction may be carried out in the vapor or liquid phase. In an embodiment, the reaction may take place at a temperature in the range of from about 7° C. to about 377° C., depending on the reactivity of the carbonyl group.

The condensation catalyst will generally be a catalyst capable of forming longer chain compounds by linking two molecules through a new carbon-carbon bond, such as a basic catalyst, a multi-functional catalyst having both acid and base functionality, or either type of catalyst also comprising an optional metal functionality. In an embodiment, the multi-functional catalyst will be a catalyst having both a strong acid and a strong base functionality. In an embodiment, aldol catalysts can comprise Li, Na, K, Cs, B, Rb, Mg, Ca, Sr, Si, Ba, Al, Zn, Ce, La, Y, Sc, Y, Zr, Ti, hydrotalcite, zinc-aluminate, phosphate, base-treated aluminosilicate zeolite, a basic resin, basic nitride, alloys or any combination thereof. In an embodiment, the base catalyst can also comprise an oxide of Ti, Zr, V, Nb, Ta, Mo, Cr, W, Mn, Re, Al, Ga, In, Co, Ni, Si, Cu, Zn, Sn, Cd, Mg, P, Fe, or any combination thereof. In an embodiment, the condensation catalyst comprises a mixed-oxide base catalysts. Suitable mixed-oxide base catalysts can comprise a combination of magnesium, zirconium, and oxygen, which may comprise, without limitation: Si—Mg—O, Mg—Ti—O, Y—Mg—O, Y—Zr—O, Ti—Zr—O, Ce—Zr—O, Ce—Mg—O, Ca—Zr—O, La—Zr—O, B—Zr—O, La—Ti—O, B—Ti—O, and any combinations thereof. Different atomic ratios of Mg/Zr or the combinations of various other elements constituting the mixed oxide catalyst may be used ranging from about 0.01 to about 50. In an embodiment, the condensation catalyst further includes a metal or alloys comprising metals, such as Cu, Ag, Au, Pt, Ni, Fe, Co, Ru, Zn, Cd, Ga, In, Rh, Pd, Ir, Re, Mn, Cr, Mo, W, Sn, Bi, Pb, Os, alloys and combinations thereof. Such metals may be preferred when a dehydrogenation reaction is to be carried out in concert with the aldol condensation reaction. In an embodiment, preferred Group IA materials include Li, Na, K, Cs and Rb. In an embodiment, preferred Group IIA materials include Mg, Ca, Sr and Ba. In an embodiment, Group IIB materials include Zn and Cd. In an embodiment, Group IIIB materials include Y and La. Basic resins include resins that exhibit basic functionality. The base catalyst may be self-supporting or adhered to any one of the supports further described below, including supports containing carbon, silica, alumina, zirconia, titania, vanadia, ceria, nitride, boron nitride, heteropolyacids, alloys and mixtures thereof.

In one embodiment, the condensation catalyst is derived from the combination of MgO and $Al_2O_3$ to form a hydrotalcite material. Another preferred material contains ZnO and $Al_2O_3$ in the form of a zinc aluminate spinel. Yet another preferred material is a combination of ZnO, $Al_2O_3$, and CuO. Each of these materials may also contain an additional metal function provided by a Group VIIIB metal, such as Pd or Pt. Such metals may be preferred when a dehydrogenation reaction is to be carried out in concert with the aldol condensation reaction. In one embodiment, the base catalyst is a metal oxide containing Cu, Ni, Zn, V, Zr, or mixtures thereof. In another embodiment, the base catalyst is a zinc aluminate metal containing Pt, Pd Cu, Ni, or mixtures thereof.

Preferred loading of the primary metal in the condensation catalyst is in the range of 0.10 wt % to 25 wt %, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second metal, if any, is in the range of 0.25-to-1 to 10-to-1, including ratios there between, such as 0.50, 1.00, 2.50, 5.00, and 7.50-to-1.

In some embodiments, the base catalyzed condensation reaction is performed using a condensation catalyst with both an acid and base functionality. The acid-aldol condensation catalyst may comprise hydrotalcite, zinc-aluminate, phosphate, Li, Na, K, Cs, B, Rb, Mg, Si, Ca, Sr, Ba, Al, Ce, La, Sc, Y, Zr, Ti, Zn, Cr, or any combination thereof. In further embodiments, the acid-base catalyst may also include one or more oxides from the group of Ti, Zr, V, Nb, Ta, Mo, Cr, W, Mn, Re, Al, Ga, In, Fe, Co, Ir, Ni, Si, Cu, Zn, Sn, Cd, P, and combinations thereof. In an embodiment, the acid-base catalyst includes a metal functionality provided by Cu, Ag, Au, Pt, Ni, Fe, Co, Ru, Zn, Cd, Ga, In, Rh, Pd, Ir, Re, Mn, Cr, Mo, W, Sn, Os, alloys or combinations thereof. In one embodiment, the catalyst further includes Zn, Cd or phosphate. In one embodiment, the condensation catalyst is a metal oxide containing Pd, Pt, Cu or Ni, and even more preferably an aluminate or zirconium metal oxide containing Mg and Cu, Pt, Pd or Ni. The acid-base catalyst may also include a hydroxyapatite (HAP) combined with any one or more of the above metals. The acid-base catalyst may be self-supporting or adhered to any one of the supports further described below, including supports containing carbon, silica, alumina, zirconia, titania, vanadia, ceria, nitride, boron nitride, heteropolyacids, alloys and mixtures thereof.

In an embodiment, the condensation catalyst may also include zeolites and other microporous supports that contain Group IA compounds, such as Li, NA, K, Cs and Rb. Preferably, the Group IA material is present in an amount less than that required to neutralize the acidic nature of the support. A metal function may also be provided by the addition of group VIIIB metals, or Cu, Ga, In, Zn or Sn. In one embodiment, the condensation catalyst is derived from the combination of MgO and $Al_2O_3$ to form a hydrotalcite material. Another preferred material contains a combination of MgO and $ZrO_2$, or a combination of ZnO and $Al_2O_3$. Each of these materials may also contain an additional metal function provided by copper or a Group VIIIB metal, such as Ni, Pd, Pt, or combinations of the foregoing.

If a Group IIB, VIB, VIIB, VIIIB, IIA or IVA metal is included in the condensation catalyst, the loading of the metal is in the range of 0.10 wt % to 10 wt %, with weight percentages of 0.10% and 0.05% increments between, such as 1.00%, 1.10%, 1.15%, 2.00%, 2.50%, 5.00% and 7.50%, etc. If a second metal is included, the preferred atomic ratio of the second metal is in the range of 0.25-to-1 to 5-to-1, including ratios there between, such as 0.50, 1.00, 2.50 and 5.00-to-1.

The condensation catalyst may be self-supporting (i.e., the catalyst does not need another material to serve as a support), or may require a separate support suitable for suspending the catalyst in the reactant stream. One exemplary support is silica, especially silica having a high surface area (greater than 100 square meters per gram), obtained by sol-gel synthesis, precipitation, or fuming. In other embodiments, particularly when the condensation catalyst is a powder, the catalyst system may include a binder to assist in forming the catalyst into a desirable catalyst shape. Applicable forming processes include extrusion, pelletization, oil dropping, or other known processes. Zinc oxide, alumina, and a peptizing agent may also be mixed together and extruded to produce a formed material. After drying, this material is calcined at a temperature appropriate for formation of the catalytically active phase, which usually requires temperatures in excess of 452° C. Other catalyst supports as known to those of ordinary skill in the art may also be used.

In some embodiments, a dehydration catalyst, a dehydrogenation catalyst, and the condensation catalyst can be present in the same reactor as the reaction conditions overlap to some degree. In these embodiments, a dehydration reaction and/or a dehydrogenation reaction may occur substantially simultaneously with the condensation reaction. In some embodiments, a catalyst may comprise active sites for a dehydration reaction and/or a dehydrogenation reaction in addition to a condensation reaction. For example, a catalyst may comprise active metals for a dehydration reaction and/or a dehydrogenation reaction along with a condensation reaction at separate sites on the catalyst or as alloys. Suitable active elements can comprise any of those listed above with respect to the dehydration catalyst, dehydrogenation catalyst, and the condensation catalyst. Alternately, a physical mixture of dehydration, dehydrogenation, and condensation catalysts could be employed. While not intending to be limited by theory, it is believed that using a condensation catalyst comprising a metal and/or an acid functionality may assist in pushing the equilibrium limited aldol condensation reaction towards completion. Advantageously, this can be used to effect multiple condensation reactions with dehydration and/or dehydrogenation of intermediates, in order to form (via condensation, dehydration, and/or dehydrogenation) higher molecular weight oligomers as desired to produce jet or diesel fuel.

The specific C4+ compounds produced in the condensation reaction will depend on various factors, including, without limitation, the type of oxygenated intermediates in the reactant stream, condensation temperature, condensation pressure, the reactivity of the catalyst, and the flow rate of the reactant stream as it affects the space velocity, GHSV and WHSV. Preferably, the reactant stream is contacted with the condensation catalyst at a WHSV that is appropriate to produce the desired hydrocarbon products. The WHSV is preferably at least about 0.1 grams of oxygenated intermediates in the reactant stream per hour, more preferably the WHSV is between about 0.1 to 40.0 g/g hr, including a WHSV of about 1, 2, 3, 4, 5, 6, 7, 8, 9, 10, 11, 12, 13, 14, 15, 20, 25, 30, 35 g/g hr, and increments between.

In general, the condensation reaction should be carried out at a temperature at which the thermodynamics of the proposed reaction are favorable. For condensed phase liquid reactions, the pressure within the reactor must be sufficient to maintain at least a portion of the reactants in the condensed liquid phase at the reactor inlet. For vapor phase reactions, the reaction should be carried out at a temperature where the vapor pressure of the oxygenates is at least about 10 kPa, and the thermodynamics of the reaction are favorable. The condensation temperature will vary depending upon the specific oxygenated intermediates used, but is generally in the range of from about 77° C. to 502° C. for reactions taking place in the vapor phase, and more preferably from about 127° C. to 452° C. For liquid phase reactions, the condensation temperature may be from about 7° C. to 477° C., and the condensation pressure from about 0.1 kPa to 10,000 kPa. Preferably, the condensation temperature is between about 17° C. and 302° C., or between about 17° C. and 252° C. for difficult substrates.

Varying the factors above, as well as others, will generally result in a modification to the specific composition and yields of the C4+ compounds. For example, varying the temperature and/or pressure of the reactor system, or the particular catalyst formulations, may result in the production of C4+ alcohols and/or ketones instead of C4+ hydrocarbons. The C4+ hydrocarbon product may also contain a variety of olefins, and alkanes of various sizes (typically branched alkanes). Depending upon the condensation catalyst used, the hydrocarbon product may also include aromatic and cyclic hydrocarbon compounds. The C4+ hydrocarbon product may also contain undesirably high levels of olefins, which may lead to coking or deposits in combustion engines, or other undesirable hydrocarbon products. In such event, the hydrocarbon molecules produced may be optionally hydrogenated to reduce the ketones to alcohols and hydrocarbons, while the alcohols and unsaturated hydrocarbon may be reduced to alkanes, thereby forming a more desirable hydrocarbon product having low levels of olefins, aromatics or alcohols.

The condensation reactions may be carried out in any reactor of suitable design, including continuous-flow, batch, semi-batch or multi-system reactors, without limitation as to design, size, geometry, flow rates, etc. The reactor system may also use a fluidized catalytic bed system, a swing bed system, fixed bed system, a moving bed system, or a combination of the above. In some embodiments, bi-phasic (e.g., liquid-liquid) and tri-phasic (e.g., liquid-liquid-solid) reactors may be used to carry out the condensation reactions.

In a continuous flow system, the reactor system can include an optional dehydrogenation bed adapted to produce dehydrogenated oxygenated intermediates, an optional dehydration bed adapted to produce dehydrated oxygenated intermediates, and a condensation bed to produce C4+ compounds from the oxygenated intermediates. The dehydrogenation bed is configured to receive the reactant stream and produce the desired oxygenated intermediates, which may have an increase in the amount of carbonyl-containing compounds. The de-hydration bed is configured to receive the reactant stream and produce the desired oxygenated intermediates. The condensation bed is configured to receive the oxygenated intermediates for contact with the condensation catalyst and production of the desired C4+ compounds. For systems with one or more finishing steps, an additional reaction bed for conducting the finishing process or processes may be included after the condensation bed.

In an embodiment, the optional dehydration reaction, the optional dehydrogenation reaction, the optional ketonization reaction, the optional ring opening reaction, and the condensation reaction catalyst beds may be positioned within the same reactor vessel or in separate reactor vessels in fluid communication with each other. Each reactor vessel preferably includes an outlet adapted to remove the product stream from the reactor vessel. For systems with one or more finishing steps, the finishing reaction bed or beds may be within the same reactor vessel along with the condensation bed or in a separate reactor vessel in fluid communication with the reactor vessel having the condensation bed.

In an embodiment, the reactor system also includes additional outlets to allow for the removal of portions of the reactant stream to further advance or direct the reaction to the desired reaction products, and to allow for the collection and recycling of reaction byproducts for use in other portions of the system. In an embodiment, the reactor system also includes additional inlets to allow for the introduction of supplemental materials to further advance or direct the reaction to the desired reaction products, and to allow for the recycling of reaction byproducts for use in other reactions.

In an embodiment, the reactor system also includes elements which allow for the separation of the reactant stream into different components which may find use in different reaction schemes or to simply promote the desired reactions. For instance, a separator unit, such as a phase separator, extractor, purifier or distillation column, may be installed prior to the condensation step to remove water from the reactant stream for purposes of advancing the condensation reaction to favor the production of higher hydrocarbons. In an embodiment, a separation unit is installed to remove specific intermediates to allow for the production of a desired product stream containing hydrocarbons within a particular carbon number range, or for use as end products or in other systems or processes.

The condensation reaction can produce a broad range of compounds with carbon numbers ranging from C4 to C30 or greater. Exemplary compounds include, but are not limited to, C4+ alkanes, C4+ alkenes, C5+ cycloalkanes, C5+ cycloalkenes, aryls, fused aryls, C4+ alcohols, C4+ ketones, and mixtures thereof. The C4+ alkanes and C4+ alkenes may range from 4 to 30 carbon atoms (C4-C30 alkanes and C4-C30 alkenes) and may be branched or straight chained alkanes or alkenes. The C4+ alkanes and C4+ alkenes may also include fractions of C7-C14, C12-C24 alkanes and alkenes, respectively, with the C7-C14 fraction directed to jet fuel blend, and the C12-C24 fraction directed to a diesel fuel blend and other industrial applications. Examples of various C4+ alkanes and C4+ alkenes include, without limitation, butane, butene, pentane, pentene, 2-methylbutane, hexane, hexene, 2-methylpentane, 3-methylpentane, 2,2-dimethylbutane, 2,3-dimethylbutane, heptane, heptene, octane, octene, 2,2,4,-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecene, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

The C5+ cycloalkanes and C5+ cycloalkenes have from 5 to 30 carbon atoms and may be unsubstituted, mono-substituted or multi-substituted. In the case of mono-substituted and multi-substituted compounds, the substituted group may include a branched C3+ alkyl, a straight chain C1+ alkyl, a branched C3+ alkylene, a straight chain C1+ alkylene, a straight chain C2+ alkylene, a phenyl or a combination thereof. In one embodiment, at least one of the substituted groups include a branched C3-C12 alkyl, a straight chain C1-C12 alkyl, a branched C3-C12 alkylene, a straight chain C1-C12 alkylene, a straight chain C2-C12 alkylene, a phenyl or a combination thereof. In yet another embodiment, at least one of the substituted groups includes a branched C3-C4 alkyl, a straight chain C1-C4 alkyl, a branched C3-C4 alkylene, a straight chain C1-C4 alkylene, a straight chain C2-C4 alkylene, a phenyl, or any combination thereof. Examples of desirable C5+ cycloalkanes and C5+ cycloalkenes include, without limitation, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, and isomers thereof.

Aryls will generally consist of an aromatic hydrocarbon in either an unsubstituted (phenyl), mono-substituted or multi-substituted form. In the case of mono-substituted and multi-substituted compounds, the substituted group may include a branched C3+ alkyl, a straight chain C1+ alkyl, a branched C3+ alkylene, a straight chain C2+ alkylene, a phenyl or a combination thereof. In one embodiment, at least one of the substituted groups includes a branched C3-C12 alkyl, a straight chain C1-C12 alkyl, a branched C3-C12 alkylene, a straight chain C2-C12 alkylene, a phenyl, or any combination thereof. In yet another embodiment, at least one of the substituted groups includes a branched C3-C4 alkyl, a straight chain C1-C4 alkyl, a branched C3-C4 alkylene, straight chain C2-C4 alkylene, a phenyl, or any combination thereof. Examples of various aryls include, without limitation, benzene, toluene, xylene (dimethylbenzene), ethyl benzene, para xylene, meta xylene, ortho xylene, C9 aromatics.

Fused aryls will generally consist of bicyclic and polycyclic aromatic hydrocarbons, in either an unsubstituted, mono-substituted or multi-substituted form. In the case of mono-substituted and multi-substituted compounds, the substituted group may include a branched C3+ alkyl, a straight chain C1+ alkyl, a branched C3+ alkylene, a straight chain C2+ alkylene, a phenyl or a combination thereof. In another embodiment, at least one of the substituted groups includes a branched C3-C4 alkyl, a straight chain C1-C4 alkyl, a branched C3-C4 alkylene, a straight chain C2-C4 alkylene, a phenyl, or any combination thereof. Examples of various fused aryls include, without limitation, naphthalene, anthracene, tetrahydronaphthalene, and decahydronaphthalene, indane, indene, and isomers thereof.

The moderate fractions, such as C7-C14, may be separated for jet fuel, while heavier fractions, (e.g., C12-C24), may be separated for diesel use. The heaviest fractions may be used as lubricants or cracked to produce additional gasoline and/or diesel fractions. The C4+ compounds may also find use as industrial chemicals, whether as an intermediate or an end product. For example, the aryls toluene, xylene, ethyl benzene, para xylene, meta xylene, ortho xylene may find use as chemical intermediates for the production of plastics and other products. Meanwhile, the C9 aromatics and fused aryls, such as naphthalene, anthracene, tetrahydronaphthalene, and decahydronaphthalene, may find use as solvents in industrial processes.

In an embodiment, additional processes are used to treat the fuel blend to remove certain components or further conform the fuel blend to a diesel or jet fuel standard. Suitable techniques include hydrotreating to reduce the amount of or remove any remaining oxygen, sulfur, or nitrogen in the fuel blend. The conditions for hydrotreating a hydrocarbon stream are known to one of ordinary skill in the art.

In an embodiment, hydrogenation is carried out in place of or after the hydrotreating process to saturate at least some olefinic bonds. In some embodiments, a hydrogenation reaction may be carried out in concert with the aldol condensation reaction by including a metal functional group with the aldol condensation catalyst. Such hydrogenation may be performed to conform the fuel blend to a specific fuel standard (e.g., a diesel fuel standard or a jet fuel standard). The hydrogenation of the fuel blend stream can be carried out according to known procedures, either with the continuous or batch method. The hydrogenation reaction may be used to remove a remaining carbonyl group or hydroxyl group. In such event, any one of the hydrogenation catalysts described above may be used. Such catalysts may include any one or more of the following metals, Cu, Ni, Fe, Co, Ru, Pd, Rh, Pt, Ir, Os, alloys or combinations thereof, alone or with promoters such as Au, Ag, Cr, Zn, Mn, Sn, Cu, Bi, and alloys thereof, may be used in various loadings ranging from about 0.01 wt % to about 20 wt % on a support as described above. In general, the finishing step is carried out at finishing temperatures of between about 80° C. to 250° C., and finishing pressures in the range of about 5 to 150 bar. In one embodiment, the finishing step is conducted in the vapor phase or liquid phase, and uses in situ generated $H_2$ (e.g., generated in the HYDROGENOLYSIS reaction step), external $H_2$, recycled $H_2$, or combinations thereof, as necessary.

In an embodiment, isomerization is used to treat the fuel blend to introduce a desired degree of branching or other shape selectivity to at least some components in the fuel blend. It may be useful to remove any impurities before the hydrocarbons are contacted with the isomerization catalyst. The isomerization step comprises an optional stripping step, wherein the fuel blend from the oligomerization reaction may be purified by stripping with water vapor or a suitable gas such as light hydrocarbon, nitrogen or hydrogen. The optional stripping step is carried out in a counter-current manner in a unit upstream of the isomerization catalyst, wherein the gas and liquid are contacted with each other, or before the actual isomerization reactor in a separate stripping unit utilizing counter-current principle.

After the optional stripping step the fuel blend can be passed to a reactive isomerization unit comprising one or several catalyst bed(s). The catalyst beds of the isomerization step may operate either in co-current or counter-current manner. In the isomerization step, the pressure may vary from 2000 kPa to 15,000 kPa, preferably in the range of 2000 kPa to 10,000 kPa, the temperature being between 197° C. and 502° C., preferably between 302° C. and 402° C. In the isomerization step, any isomerization catalysts known in the art may be used. Suitable isomerization catalysts can contain molecular sieve and/or a metal from Group VII and/or a carrier. In an embodiment, the isomerization catalyst contains SAPO-11 or SAPO41 or ZSM-22 or ZSM-23 or ferrierite and Pt, Pd or Ni and $Al_2O_3$ or $SiO_2$. Typical isomerization catalysts are, for example, Pt/SAPO-11/$Al_2O_3$, Pt/ZSM-22/$Al_2O_3$, Pt/ZSM-23/$Al_2O_3$ and Pt/SAPO-11/$SiO_2$.

Other factors, such as the concentration of water or undesired oxygenated intermediates, may also effect the composition and yields of the C4+ compounds, as well as the activity and stability of the condensation catalyst. In such event, the process may include a dewatering step that removes a portion of the water prior to the condensation reaction and/or the optional dehydration reaction, or a separation unit for removal of the undesired oxygenated intermediates. For instance, a separator unit, such as a phase separator, extractor, purifier or distillation column, may be installed prior to the condensation step so as to remove a portion of the water from the reactant stream containing the oxygenated intermediates. A separation unit may also be installed to remove specific oxygenated intermediates to allow for the production of a desired product stream containing hydrocarbons within a particular carbon range, or for use as end products or in other systems or processes.

Thus, in one embodiment, the fuel blend produced by the processes described herein is a hydrocarbon mixture that meets the requirements for jet fuel (e.g., conforms with ASTM D1655). In another embodiment, the product of the processes described herein is a hydrocarbon mixture that comprises a fuel blend meeting the requirements for a diesel fuel (e.g., conforms with ASTM D975).

Yet in another embodiment of the invention, the C2+ olefins are produced by catalytically reacting the oxygenated intermediates in the presence of a dehydration catalyst at a dehydration temperature and dehydration pressure to produce a reaction stream comprising the C2+ olefins. The C2+ olefins comprise straight or branched hydrocarbons containing one or more carbon-carbon double bonds. In general, the C2+ olefins contain from 2 to 8 carbon atoms, and more preferably from 3 to 5 carbon atoms. In one embodiment, the olefins comprise propylene, butylene, pentylene, isomers of the foregoing, and mixtures of any two or more of the foregoing. In another embodiment, the C2+ olefins include C4+ olefins produced by catalytically reacting a portion of the C2+ olefins over an olefin isomerization catalyst. In an embodiment, a method of forming a fuel blend from a biomass feedstock may comprise a digester that receives a biomass feedstock and a digestive solvent operating under conditions to effectively remove nitrogen and sulfur compounds from said biomass feedstock and discharges a treated stream comprising a carbohydrate having less than 35% of the sulfur content and less than 35% of the nitrogen content of the untreated biomass feedstock on a dry mass basis; an hydrogenolysis and hydrodeoxygenation reactor comprising an hydrogenolysis and hydrodeoxygenation catalyst that receives the treated stream and discharges an oxygenated intermediate, wherein a first portion of the oxygenated intermediate stream is recycled to the digester as at least a portion of the digestive solvent; a first fuels processing reactor comprising a dehydrogenation catalyst that receives a second portion of the oxygenated intermediate stream and discharges an olefin-containing stream; and a second fuels processing reactor comprising an alkylation catalyst that receives the olefin-containing stream and discharges a liquid fuel.

The dehydration catalyst comprises a member selected from the group consisting of an acidic alumina, aluminum phosphate, silica-alumina phosphate, amorphous silica-alumina, aluminosilicate, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, and a combination of any two or more of the foregoing. In one embodiment, the dehydration catalyst further comprises a modifier selected from the group consisting of Ce, Y, Sc, La, Li, Na, K, Rb, Cs, Mg, Ca, Sr, Ba, P, B, Bi, and a combination of any two or more of the foregoing. In another embodiment, the dehydration catalyst further comprises an oxide of an element, the element selected from the group consisting of Ti, Zr, V, Nb, Ta, Mo, Cr, W, Mn, Re, Al, Ga, In, Fe, Co, Ir, Ni, Si, Cu, Zn, Sn, Cd, P, and a combination of any two or more of the foregoing. In yet another embodiment, the dehydration catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

In yet another embodiment, the dehydration catalyst comprises an aluminosilicate zeolite. In one version, the dehydration catalyst further comprises a modifier selected from the group consisting of Ga, In, Zn, Fe, Mo, Ag, Au, Ni, P, Sc, Y, Ta, a lanthanide, and a combination of any two or more of the foregoing. In another version, the dehydration catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

In another embodiment, the dehydration catalyst comprises a bifunctional pentasil ring-containing aluminosilicate zeolite. In one version, the dehydration catalyst further comprises a modifier selected from the group consisting of Ga, In, Zn, Fe, Mo, Ag, Au, Ni, P, Sc, Y, Ta, a lanthanide, and a combination of any two or more of the foregoing. In another version, the dehydration catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing.

The dehydration reaction is conducted at a temperature and pressure where the thermodynamics are favorable. In general, the reaction may be performed in the vapor phase, liquid phase, or a combination of both. In one embodiment, the dehydration temperature is in the range of about 100° C. to 500° C., and the dehydration pressure is in the range of about 0 to 100 bar. In another embodiment, the dehydration temperature is in the range of about 125° C. to 450° C., and the dehydration pressure is at least 0.1 bar absolute. In another version, the dehydration temperature is in the range of about 150° C. to 350° C., and the dehydration pressure is in the range of about 5 to 50 bar. In yet another version, the dehydration temperature is in the range of about 175° C. to 325° C.

The C6+ paraffins are produced by catalytically reacting the C2+ olefins with a stream of C4+ isoparaffins in the presence of an alkylation catalyst at an alkylation temperature and alkylation pressure to produce a product stream comprising C6+ paraffins. The C4+ isoparaffins include alkanes and cycloalkanes having 4 to 7 carbon atoms, such as isobutane, isopentane, naphthenes, and higher homologues having a tertiary carbon atom (e.g., 2-methylbutane and 2,4-dimethylpentane), isomers of the foregoing, and mixtures of any two or more of the foregoing. In one embodiment, the stream of C4+ isoparaffins comprises of internally generated C4+ isoparaffins, external C4+ isoparaffins, recycled C4+ isoparaffins, or combinations of any two or more of the foregoing.

The C6+ paraffins will generally be branched paraffins, but may also include normal paraffins. In one version, the C6+ paraffins comprises a member selected from the group consisting of a branched C6-10 alkane, a branched C6 alkane, a branched C7 alkane, a branched C8 alkane, a branched C9 alkane, a branched $C_{10}$ alkane, or a mixture of any two or more of the foregoing. In one version, the C6+ paraffins comprise dimethylbutane, 2,2-dimethylbutane, 2,3-dimethylbutane, methylpentane, 2-methylpentane, 3-methylpentane, dimethylpentane, 2,3-dimethylpentane, 2,4-dimethylpentane, methylhexane, 2,3-dimethylhexane, 2,3,4-trimethylpentane, 2,2,4-trimethylpentane, 2,2,3-trimethylpentane, 2,3,3-trimethylpentane, dimethylhexane, or mixtures of any two or more of the foregoing.

The alkylation catalyst comprises a member selected from the group of sulfuric acid, hydrofluoric acid, aluminum chloride, boron trifluoride, solid phosphoric acid, chlorided alumina, acidic alumina, aluminum phosphate, silica-alumina phosphate, amorphous silica-alumina, aluminosilicate, aluminosilicate zeolite, zirconia, sulfated zirconia, tungstated zirconia, tungsten carbide, molybdenum carbide, titania, sulfated carbon, phosphated carbon, phosphated silica, phosphated alumina, acidic resin, heteropolyacid, inorganic acid, and a combination of any two or more of the foregoing. The alkylation catalyst may also include a mixture of a mineral acid with a Friedel-Crafts metal halide, such as aluminum bromide, and other proton donors.

In one embodiment, the alkylation catalyst comprises an aluminosilicate zeolite. In one version, the alkylation catalyst further comprises a modifier selected from the group consisting of Ga, In, Zn, Fe, Mo, Ag, Au, Ni, P, Sc, Y, Ta, a lanthanide, and a combination of any two or more of the foregoing. In another version, the alkylation catalyst further comprises a metal selected from the group consisting of Cu, Ag, Au, Pt, Ni, Fe, Co, Ru, Zn, Cd, Ga, In, Rh, Pd, Ir, Rr, Mn, Cr, Mo, W, Sn, Os, an alloy of any two or more of the foregoing, and a combination of any two or more of the foregoing.

In another embodiment, the alkylation catalyst comprises a bifunctional pentasil ring-containing aluminosilicate zeolite. In one version, the alkylation catalyst further comprises a modifier selected from the group consisting of Ga, In, Zn, Fe, Mo, Ag, Au, Ni, P, Sc, Y, Ta, a lanthanide, and a combination of any two or more of the foregoing. In another version, the alkylation catalyst further comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy of any two or more of the foregoing, and a combination of any two or more of the foregoing. In one version, the dehydration catalyst and the alkylation catalyst are atomically identical.

The alkylation reaction is conducted at a temperature where the thermodynamics are favorable. In general, the alkylation temperature is in the range of about −20° C. to 300° C., and the alkylation pressure is in the range of about 0 psig to 200 bar. In one version, the alkylation temperature is in the range of about 100° C. to 300° C. In another version, the alkylation temperature is in the range of about 0° C. to 100° C., and the alkylation pressure is at least 5 bar. In yet another version, the alkylation temperature is in the range of about 0° C. to 50° C. and the alkylation pressure is less than 20 bar. In still yet another version, the alkylation temperature is in the range of about 70° C. to 250° C., and the alkylation pressure is in the range of about 5 to 100 bar. In one embodiment, the alkylation catalyst comprises a mineral acid or a strong acid and the alkylation temperature is less than ° C. In another embodiment, the alkylation catalyst comprises a zeolite and the alkylation temperature is greater than 100° C.

Another aspect of the present invention is that the C4+ isoparaffins may be generated internally by catalytically reacting an isoparaffin feedstock stream comprising C4+ normal paraffins, aromatics and/or naphthenes in the presence of an isomerization catalyst at an isomerization temperature and isomerization pressure to produce internally generated C4+ isoparaffins. The C4+ normal paraffins will generally include alkanes having 4 to 7 carbon atoms, such as n-butane, n-pentane, n-hexane, n-heptane, and mixtures of any two or more of the foregoing. In one arrangement, the isoparaffin feedstock stream is collected upstream of the alkylation catalyst from the reaction stream having the oxygenated intermediates or the reaction stream having the C2+ olefins and processed for the production of the internally generated C4+ isoparaffins. In another arrangement, the C4+ normal paraffins, aromatics and/or naphthenes are collected downstream of the alkylation catalyst from the product stream having the C6+ paraffins and then recycled for use in the production of the internally generated $C_{4+}$ isoparaffins. The C4+ isoparaffins may also be provided solely from an external source or used to supplement the internally generated C4+ isoparaffins. In another version, the C4+ isoparaffins are recycled C4+ isoparaffins collected from the product stream having the C6+ paraffins.

The isomerization catalyst is a catalyst capable of reacting a C4+ normal paraffin, aromatic or naphthene to produce a C4+ isoparaffin. In one version, the isomerization catalyst includes a zeolite, zirconia, sulfated zirconia, tungstated zirconia, alumina, silica-alumina, zinc aluminate, chlorided alumina, phosphoric acid, or mixtures of any two or more of the foregoing. In another version, the isomerization catalyst is an acidic beta, mordenite, or ZSM-5 zeolite. In yet another version, the isomerization catalyst further comprises a metal selected from the group consisting of Y, Pt, Ru, Ad, Ni, Rh, Ir, Fe, Co, Os, Zn, a lanthanide, or an alloy or combination of any two or more of the foregoing. In still yet another version, the isomerization catalyst comprises a support, the support comprising alumina, sulfated oxide, clay, silica gel, aluminum phosphate, bentonite, kaolin, magnesium silicate, magnesium carbonate, magnesium oxide, aluminum oxide, activated alumina, bauxite, silica, silica-alumina, activated carbon, pumice, zirconia, titania, zirconium, titanium, kieselguhr, or zeolites.

In an embodiment of the present invention, the fuel yield of the current process may be greater than other bio-based feedstock conversion processes. Without wishing to be limited by theory, it is believed that substantially removing nitrogen compounds and sulfur compounds from the soluble carbohydrate prior to the direct hydrogenolysis allows for a greater percentage of the biomass to be converted into higher hydrocarbons while limiting the formation of degradation products.

To facilitate a better understanding of the present invention, the following examples of certain aspects of some embodiments are given. In no way should the following examples be read to limit, or define, the entire scope of the invention.

EXAMPLES

Reaction studies were conducted in a Parr5000 Hastelloy multireactor comprising 6×75-milliliter reactors operated in parallel at pressures up to 135 bar, and temperatures up to 275° C., stirred by magnetic stir bar. Alternate studies were conducted in 100-ml Parr4750 reactors, with mixing by top-driven stir shaft impeller, also capable of 135 bar and 275° C. Larger scale extraction, pretreatment and digestion tests were conducted in a 1-Liter Parr reactor with annular basket housing biomass feed, or with filtered dip tube for direct contacting of biomass slurries.

Reaction samples were analyzed for sugar, polyol, and organic acids using an HPLC method entailing a Bio-Rad Aminex HPX-87H column (300 mm×7.8 mm) operated at 0.6 ml/minute of a mobile phase of 5 mM Sulfuric Acid in water, at an oven temperature of 30° C., a run time of 70 minutes, and both RI and UV (320 nm) detectors.

Product formation (mono-oxygenates, glycols, diols, alkanes, acids) were monitored via a gas chromatographic (GC) method "DB5-ox", entailing a 60-m×0.32 mm ID DB-5 column of 1 um thickness, with 50:1 split ratio, 2 ml/min helium flow, and column oven at 40° C. for 8 minutes, followed by ramp to 285° C. at 10° C./min, and a hold time of 53.5 minutes. Injector temperature is set at 250° C., and detector temperature at 300° C.

Gasoline production potential by condensation was assessed via injection of one microliters of liquid intermediate product into a catalytic pulse microreactor entailing a GC insert packed with 0.12 grams of ZSM-5 catalyst, held at 375° C., followed by Restek Rtx-1701 (60-m) and DB-5 (60-m) capillary GC columns in series (120-m total length, 0.32 mm ID, 0.25 um film thickness) for an Agilent/HP 6890 GC equipped with flame ionization detector. Helium flow was 2.0 ml/min (constant flow mode), with a 10:1 split ratio. Oven temperature was held at 35° C. for 10 minutes, followed by a ramp to 270° C. at 3° C./min, followed by a 1.67 minute hold time. Detector temperature was 300° C.

Example 1

Nickel Catalyst

A 100-ml Parr reactor was charged with 0.9243-grams of Ni-5249P catalyst (64% nickel on silica; Strem Chemicals, Inc.), 3.59-grams of milled bagasse (1-mm grate, 5% moisture), and 60.1-grams of deionized water. The reactor was pressured to 510 psig (3600 kPa) with $H_2$, before heating to 170 C for 2.5 hours, then 190 C for 2.5 hours, followed by heating to 210° C. for 22 hours.

Two additional cycles were conducted with the same temperature sequence, following addition of 3.62 and 3.58 grams of bagasse. A final pH of 3.89 was observed, indicating acid coproduct formation. Formation of 2.1 wt % acetic acid was verified via DB5-ox GC analysis. Following reaction, solids were recovered by filtration on Whatman #2 filter paper, and oven dried overnight at 90° C. to assess the extent of digestion of biomass. Greater than 98% of the total bagasse charged over three cycles was digested. Ethylene glycol (EG) and 1,2-propylene glycol (PG) comprised more than 26.4% of the hydrocarbon products, as measured via DB5-ox GC method (Table 1). The remainder of product analyzed as a mixture of primarily $C_2$-$C_6$ oxygenates (alcohols, ketones) and carboxylic acids, suitable for condensation to liquid biofuels.

TABLE 1

Bagasse Hydrogenolysis with Nickel catalyst

| Component | wt % of HC products |
|---|---|
| Ethylene glycol | 8.6 |
| 1,2-Propylene glycol | 17.8 |

TABLE 1-continued

Bagasse Hydrogenolysis with Nickel catalyst

| Component | wt % of HC products |
|---|---|
| Glycerol | 5.7 |
| Erythritol | 4.2 |
| Total polyols | 36.4 |
| Total glycols | 26.4 |

Weight percent of total hydrocarbon (HC) products.

One microliter of liquid product was injected onto the ZSM-5 pulse microreactor at 370° C. at a 1:15 split ratio to assess gasoline formation potential. Formation of alkanes, benzene, toluene, xylenes, trimethylbenzenes, and naphthalenes were observed at an approximate yield of 59% relative to that expected from complete conversion of the carbohydrate fraction of the feed bagasse. This result demonstrates co-production of glycols and liquid biofuels via direct hydrogenolysis of biomass, followed by acid-catalyzed condensation of oxygenates present in the hydrogenolysis product stream.

Example 2

Sulfided Cobalt Molybdate Catalyst

A multi-cycle experiment was conducted using a nominal 3.50 grams of bagasse with 1.04 grams of sulfided cobalt-molybdate catalyst (DC-2533 catalyst from Criterion Catalyst & Technologies L.P) and 58.50 grams of deionized water. The catalyst was sulfided by the method described in US2010/0236988, Example 5. The Parr 100-ml reactor was pressured to 1024 psig with $H_2$ (7200 kPa), and heated to 170° C., and ramped to 240° C. over 7 hours, before holding at 240° C. overnight to completed an initial cycle. Four additional cycles were completed in subsequent 24-hour periods, entailing 9-hour ramps from 160-250° C., before holding at 250° C. overnight. A total of 17.59 grams of bagasse were charged for the five cycles.

A final pH of 3.49 was measured, indicated acid formation from the biomass feed. DB5-ox GC analysis indicated 1.67% acetic acid present in the final reaction liquid. Following reaction, solids were recovered by filtration on Whatman #2 filter paper, and oven dried overnight at 90° C. to assess the extent of digestion of biomoass. Results indicaed 73% of the total bagasse charged over was digested into liquid soluble products. Ethylene glycol (10.8%) and 1,2-propylene glycol (14.9%) comprised more than 25.7% of the hydrocarbon products, as measured via DB5-ox GC method (Table 2). The remainder of product analyzed as a mixture of primarily C2-C6 oxygenates (alcohols, ketones), and carboxylic acids, suitable for condensation to liquid biofuels.

Liquid product was injected onto the ZSM-5 pulse microreactor at 375° C. to assess gasoline formation potential. Formation of alkanes, benzene, toluene, xylenes, trimethylbenzenes, and naphthalenes were observed at an approximate yield of 36% relative to that expected from complete conversion of the carbohydrate fraction of the feed bagasse. This result demonstrates co-production of glycols and liquid biofuels via direct hydrogenolysis of biomass over sulfided cobalt-molybdate catalyst, followed by acid-catalyzed condensation of oxygenates present in the hydrogenolysis product stream.

TABLE 2

Bagasse Hydrogenolysis with Sulfided Cobalt-Molybdate catalyst

| Component | Wt % of Total HC products |
|---|---|
| Ethylene glycol | 10.8 |
| 1,2-Propylene glycol | 14.9 |
| Glycerol | 6.6 |
| Erythritol | 11.7 |
| Total polyols | 44.0 |
| Total glycols | 25.7 |

Example 3

Use of Calcium Carbonate Cocatalyst/Buffer

Example 2 was repeated with addition of 2.06 grams of calcium carbonate for the initial reaction, followed by addition of 0.50-0.51 grams of calcium carbonate for each successive cycle, to maintain a pH of greater than 4.5 throughout the reaction sequence. A final pH of 4.84 was measured at the end of the fifth cycle. A total of 18.71 grams of bagasse (dry basis) were charged across the five reaction cycles.

Following reaction, solids were recovered by filtration on Whatman #2 filter paper, and oven dried overnight at 90° C. to assess the extent of digestion of biomoass. Results indicated 90% of the total bagasse charged over was digested into liquid soluble products. Ethylene glycol (9.1%) and 1,2-propylene glycol (32.8%) comprised more than 41% of the hydrocarbon products, as measured via DB5-ox GC method (Table 3). The remainder of product analyzed as a mixture of primarily C2-C6 oxygenates (alcohols, ketones), and carboxylic acids, suitable for condensation to liquid biofuels.

Liquid product was injected onto the ZSM-5 pulse microreactor at 375° C. to assess gasoline formation potential. Formation of alkanes, benzene, toluene, xylenes, trimethylbenzenes, and naphthalenes were observed at an approximate yield of 50% relative to that expected from complete conversion of the carbohydrate fraction of the feed bagasse. This result demonstrates co-production of glycols and liquid biofuels via direct hydrogenolysis of biomass over sulfided cobalt-molybdate catalyst, followed by acid-catalyzed condensation of oxygenates present in the hydrogenolysis product stream. Use of a basic buffer such as calcium carbonate to improve yields of glycols, and moderate pH, is also established.

TABLE 3

Hydrogenolysis with sulfided cobalt molybdate catalyst and calcium carbonate buffer

| Component | wt % of total HC products |
|---|---|
| Ethylene glycol | 9.1 |
| 1,2-Propylene glycol | 32.8 |
| Glycerol | 1.0 |
| Erythritol | 0.2 |
| Total polyols | 43.0 |
| Total glycols | 41.9 |

Example 4

Sulfided Cobalt Molybdate Catalyst with KOH Buffer

Experiment 2 was repeated with addition of 1N KOH to buffer pH to 5.5 for each reaction step. Three reaction cycles were conducted with addition of 10.03 grams of bagasse (dry basis). A final pH of 5.34 was measured for the liquid product of three cycles.

Following reaction, solids were recovered by filtration on Whatman #2 filter paper, and oven dried overnight at 90° C. to assess the extent of digestion of biomoass. Results indicated 87.9% of the total bagasse charged over was digested into liquid soluble products. Ethylene glycol (5.1%) and 1,2-propylene glycol (16.7%) comprised more than 21% of the hydrocarbon products, as measured via DB5-ox GC method (Table 4). Further conversion of glycerol (8.2%) to propylene glycol can be achieved via continuing the —OH hydrogenolysis reaction, resulting in higher yields of glycol products. The remainder of product analyzed as a mixture of primarily C2-C6 oxygenates (alcohols, ketones) and carboxylic acids, suitable for condensation to liquid biofuels.

Liquid product was injected onto the ZSM-5 pulse microreactor at 375° C. to assess gasoline formation potential. Formation of alkanes, benzene, toluene, xylenes, trimethylbenzenes, and naphthalenes were observed at an approximate yield of 69% relative to that expected from complete conversion of the carbohydrate fraction of the feed bagasse. This result demonstrates co-production of glycols and liquid biofuels via direct hydrogenolysis of biomass over sulfided cobalt-molybdate catalyst, followed by acid-catalyzed condensation of oxygenates present in the hydrogenolysis product stream. Use of potassium hydroxide as a basic buffer to maintain pH>5 was demonstrated to give high yields of glycol intermediate products.

TABLE 4

Bagasse Hydrogenolysis with Sulfided Cobalt Molybdate catalyst and KOH buffer

| Component | wt % of HC products |
|---|---|
| Ethylene glycol | 5.1 |
| 1,2-Propylene glycol | 16.7 |
| Glycerol | 8.2 |
| Erythritol | 12.0 |
| Total polyols | 42.0 |
| Total glycols | 21.8 |

Example 5

Hardwood Hydrogenolysis with Ruthenium Catalyst 2.037 grams of ground Northern hardwood were charged with 20.073 grams of deionized water, and 0.470 grams of 5% Ru/C Escat 4401 catalyst (Strem Chemicals, 50% wet), to a 75-ml Parr5000 reactor. The reactor was pressured to 700 psig with $H_2$, and ramped from 170-240° C. over 6 hours, before maintaining 240° C. overnight to complete reaction. The sequence was repeated for two additional cycles with addition of 1.99 and 2.09 grams of ground hardwood. Final pH measured at the end of the reaction cycles was 3.20.

Following reaction, solids were recovered by filtration on Whatman #2 filter paper, and oven dried overnight at 90° C. to assess the extent of digestion of biomoass. Results indicated 88% digestion of the hardwood charged, into liquid soluble products. Ethylene glycol (4.9%) and 1,2-propylene glycol (18.1%) comprised more than 22% of the hydrocarbon products, as measured via DB5-ox GC method (Table 5).

TABLE 5

Hardwood hydrogenolysis with Ruthenium catalyst

| Component | wt % of HC products |
|---|---|
| Ethylene glycol | 4.9 |
| 1,2-Propylene glycol | 18.1 |
| Glycerol | 4.1 |
| Erythritol | 1.1 |
| Total polyols | 28.1 |
| Total glycols | 22.9 |

Example 6

Softwood (Pine) Hydrogenolysis with Ruthenium Catalyst

The experiment of example 5 was repeated with addition of ground Southern pine as the biomass feed, and with use of a Re-promoted 1.9% Pt/zirconia catalyst at Re:Pt rato of 3.75:1 prepared according to the method in Example 7 of US2008/0215391. 6.12 grams of pine wood were added over three cycles. Final pH measured after three cycles was 3.06.

Following reaction, solids were recovered by filtration on Whatman #2 filter paper, and oven dried overnight at 90° C. to assess the extent of digestion of biomoass. Results indicated greater than 98% digestion of the hardwood charged, into liquid soluble products. Ethylene glycol (9.8%) and 1,2-propylene glycol (14.1%) comprised more than 22% of the hydrocarbon products, as measured via DB5-ox GC method (Table 6). Further conversion of glycerol (7.4%) to propylene glycol can be achieved via continuing the —OH hydrogenolysis reaction, to further increase glycol yields. The remainder of product analyzed as a mixture of primarily C2-C6 oxygenates (alcohols, ketones), and carboxylic acids, suitable for condensation to liquid biofuels.

Liquid product was injected onto the ZSM-5 pulse microreactor at 375° C. to assess gasoline formation potential. Formation of alkanes, benzene, toluene, xylenes, trimethylbenzenes, and naphthalenes were observed at an approximate yield of 30% relative to that expected from complete conversion of the carbohydrate fraction of the feed softwood.

TABLE 6

Softwood (Pine) Hydrogenolysis with Pt—Re/zirconia catalyst

| Component | wt % of HC products |
|---|---|
| Ethylene glycol | 9.8 |
| 1,2-Propylene glycol | 14.1 |
| Glycerol | 7.4 |
| Erythritol | 1.1 |
| Total polyols | 32.4 |
| Total glycols | 23.9 |

Examples 7-25

Hydrogenolysis of Sorbitol Over Nickel, Ruthenium and Cobalt Catalysts

Nickel(Strem Chemicals, Inc; Sigma-Aldrich Inc; x-Activated Metals Inc), ruthenium (Strem Chemicals, Inc), and cobalt (W.R. Grace & Co., Raney Type 2724) hydrogenolysis catalysts were examined for the hydrogenolysis of sorbitol, representative of the sugar alcohol formed from hydrolysis and hydrogenation of sugar, starch, or biomass feed to an aqueous phase refoming or hydrogenolysis reactor. Conversion of sorbitol and formation of glycol and polyol products were determined by HPLC analysis. Results show formation of glycol intermediates, with polyol yield (including glycerol) of 30-70% over the range of conditions tested. Sodium carbonate and calcium hydroxide were used to buffer pH over the range of 3-9.

FIG. 4 shows a cross plot of conversion of sorbitol, vs. selectivity to glycols including glycerol. Selectivity is improved at lower conversions of sorbitol. Selectivities observed were never greater than about 70%, which demonstrates the value of the current invention where the monoxygenates-rich stream formed as the remainder of the reaction products, is converted to value added liquid fuels. Controlling conversion from about 50% to about 80% by variation in contact time with catalyst, or temperature, allows variation in the amount of glycols formed, relative to the monooxyenate intermediates which are converted to liquid fuels. Production ratios of glycols to liquid fuels can thus be controlled, to optimize commercial economics.

TABLE 7

Hydrogenolysis with 50% Sorbitol feed over various catalysts

| Ex# | Catalyst | Base | T C | Psi H2 | Final pH | Time hours | GLY wt % | EG wt % | PG wt % | Total Polyol wt % | Sorb conv | Polyol Yield |
|---|---|---|---|---|---|---|---|---|---|---|---|---|
| 7 | Ru/C | Na₂CO₃ | 200 | 1175 | 8.88 | 19.10 | 0.00 | 1.31 | 5.16 | 18.50 | 0.76 | 0.37 |
| 8 | Ni5249P | Na₂CO₃ | 195 | 1000 | 8.81 | 23.10 | 0.00 | 2.93 | 14.13 | 17.92 | 0.98 | 0.36 |
| 9 | A7000 | Na₂CO₃ | 210 | 1010 | 5.84 | 22.00 | 1.11 | 1.72 | 4.04 | 15.27 | 0.83 | 0.31 |
| 10 | Ru/C | Na₂CO₃ | 210 | 1015 | 7.99 | 23.10 | 0.00 | 1.52 | 7.09 | 11.14 | 0.95 | 0.22 |
| 11 | RaCo2724 | Na2CO3 | 210 | 1012 | 6.03 | 22.00 | 0.70 | 1.31 | 3.22 | 17.04 | 0.76 | 0.34 |
| 12 | Ni5249P | Na2CO3 | 210 | 1010 | 7.56 | 6.75 | 0.61 | 3.65 | 9.52 | 26.99 | 0.74 | 0.54 |
| 13 | RaCo2724 | Na₂CO₃ | 210 | 1005 | 5.12 | 23.10 | 1.51 | 1.21 | 3.43 | 27.95 | 0.56 | 0.56 |
| 14 | RaNi | Ca(OH)₂ | 210 | 1300 | 4.11 | 23.80 | 1.52 | 2.13 | 4.86 | 24.73 | 0.68 | 0.49 |
| 15 | Ru/C | Ca(OH)₂ | 210 | 1009 | 4.90 | 19.60 | 2.71 | 3.70 | 11.54 | 35.04 | 0.66 | 0.70 |
| 16 | Ni5249P | Na₂CO₃ | 220 | 1272 | 5.31 | 23.60 | 0.58 | 3.84 | 17.29 | 22.50 | 0.98 | 0.45 |
| 17 | Ni5249P | Ca(OH)₂ | 210 | 1010 | 4.83 | 22.80 | 3.24 | 3.49 | 15.95 | 24.82 | 0.96 | 0.50 |
| 18 | Ni5249P | Ca(OH)₂ | 210 | 1266 | 3.96 | 7.70 | 8.03 | 3.89 | 10.36 | 33.37 | 0.78 | 0.67 |
| 19 | 5% Ru/C | Ca(OH)₂ | 210 | 1270 | 3.68 | 22.50 | 4.12 | 1.60 | 3.66 | 30.40 | 0.58 | 0.61 |
| 20 | RaNi* | Ca(OH)₂ | 220 | 798 | 3.27 | 18.50 | 2.94 | 1.82 | 4.86 | 32.85 | 0.54 | 0.66 |
| 21 | RaCo2724 | Ca(OH)₂ | 210 | 990 | 3.79 | 25.00 | 2.75 | 1.50 | 5.25 | 29.13 | 0.61 | 0.58 |
| 22 | Ni5249P | Ca(OH)₂ | 210 | 1300 | 3.79 | 20.10 | 2.61 | 3.09 | 17.10 | 23.04 | 1.00 | 0.46 |
| 23 | 5% Ru/C | Ca(OH)₂ | 220 | 992 | 3.95 | 19.00 | 3.01 | 1.81 | 5.12 | 25.59 | 0.69 | 0.51 |
| 24 | 5% Ru/C | Ca(OH)₂ | 210 | 1309 | 3.71 | 19.10 | 4.47 | 1.83 | 5.08 | 28.26 | 0.66 | 0.57 |
| 25 | Ni5249P | Ca(OH)₂ | 220 | 1255 | 3.82 | 7.40 | 4.45 | 3.24 | 14.98 | 25.89 | 0.94 | 0.52 |

Ru/C = 5% Ru/C Escat ™ 4401 catalyst (Strem Chemicals, Inc. 50% wet)

Ni5249P = 64% nickel on silica (Strem Chemicals, Inc.)

A7000 = Mo-promoted sponge metal catalyst (Activated Metals Inc.)

RaCo2724 = W R Grace & Co.: Raney cobalt

RaNi = Mo-promoted Raney-type nickel catalyst (Aldrich Chemical Company Inc.)

GLY = glycerol

Sorb = sorbitol

Example 26

Separation of Glycols from Hydrogenolysis Reaction Intermediates

A short-path distillation was conducted with 71.184 grams of a high conversion flow reaction product obtained from the hydrogenolysis at 240 C and 667 psig under co-feed of $H_2$, of 50% sorbitol over rhenium-promoted 1.9% Pt/zirconia catalyst. The flash distillation was conducted at atmospheric pressure under nitrogen, with a 2:1 reflux ratio. An initial distillation cut comprising 17.6% of the total feed, was distilled at a tops temperature of 77-79° C. An organic layer of 13.3% by volume was observed in the distilled sample. Distillation was continued until no further offtake at a tops temperature of 101° C., and a bottoms temperature of 120° C. HPLC analysis of feed and final bottoms samples are shown in Table 8. Heavy glycols and unconverted sorbitol were concentrated in the distillation bottoms, with low losses to overheads. DB5-ox analysis of mono-oxygenates and glycols indicated greater than 88% rejection of monooxygenates into the overheaded distillate relative to feed, with less than 10% of monooxygenate light ends of boiling point less than glycerol, present in final bottoms product. Further separation via via an increased number of stages can be expected to give improved separation, if desired.

TABLE 8

Rash distillation of hydrogenolysis reactor product

| Sample | Sorbitol wt % | EG wt % | PG wt % | Gly wt % | Total grams |
|---|---|---|---|---|---|
| feed | 5.37 | 1.84 | 1.39 | 1.07 | 71.184 |
| bottoms | 18.57 | 2.93 | 5.87 | 3.95 | 19.960 |
| conc ratio | 3.46 | 1.59 | 4.23 | 3.6A9 | 3.566 |

Gly = glycerol

Example 27

Separation and Purification of Glycol Co-Products

An Aspen Plus (version 2006.5) simulation (FIG. 1) was conducted for a model hydrogenolysis reaction outlet stream comprising 2-propanol, ethanol, ethylene glycol, propylene glycol, and unconverted sorbitol, simulating the crude product from hydrogenolysis of a bio-based feed stream. Separation of light alcohols, water, and glycols from unconverted sorbitol as an overhead stream was readily effected by flash separation at ambient pressure (1-5 psig). Unconverted sorbitol can be recycle to reaction. A partial flash separation with recycle of some water, sorbitol, and glycols back to reaction is preferred, to prevent sorbitol precipitation. Overheads from the flash separation comprising ethanol, 2-propanol, water, ethylene glycol, and propylene were routed to an atmospheric pressure distillation column (nominal 1-5 psig) to separate ethanol, 2-propanol, and water from ethylene glycol and propylene glycol. A 20 stage column operated at a reflux ratio of 4, with 100° C. top distillate temperature, and 189° C. bottoms temperature, effected virtual complete separation of water and light monooxygenates, from the ethylene glycol (EG) and propylene glycol (PG) product mixture. The bottoms glycol mixture from this column comprising ethylene glycol and propylene glycol could be fractionated to give a 125° C. tops distillate stream comprising 1,2-propylene glycol at greater than 99% purity, and a 139° C. bottoms stream comprising ethylene glycol at greater than 99% purity, via a 90 stage column operating at a reflux ratio of 10, and under moderate vacuum of 100 ton absolute pressure.

While many different separation sequences can be developed by those skilled in the art, the current example shows one configuration where purified ethylene glycol and propylene glycol product streams may be obtained, as separate products.

What is claimed is:

1. A process of co-producing biofuels and glycols comprising:
   (i) providing a bio-based feedstock stream containing carbohydrates and water;
   (ii) contacting, in a first reaction system, the bio-based feedstock stream with hydrogen in the presence of a hydrogenolysis catalyst at a temperature in the range of 120° C. to 280° C. and 0.1 to 150 bar of hydrogen to produce a hydrogenolysis stream containing at least 5 wt %, based on the total oxygenates content, of glycols that comprises ethylene glycol (EG) and 1,2-propylene glycol (PG), and other monooxygenates;
   (iii) contacting, in a second reaction system, at least a first portion of said hydrogenolysis stream with hydrogen in the presence of a hydrogenolysis catalyst at a temperature in the range of 160° C. to 280° C. and in the presence of 0.1 to 150bar hydrogen to produce an oxygenated intermediate stream comprising at least 5 wt %, based on the total oxygenates, of monooxygenated hydrocarbons of chain length less than 6 carbons;
   (iv) processing at least a portion of the oxygenated intermediate stream to form a liquid fuel;
   (v) providing a second portion of said hydrogenolysis stream to a first separation system;
   (vi) separating a portion of said hydrogenolysis stream, in the first separation system, to a monooxygenates stream comprising monooxygenates and a glycol rich stream comprising at least 10 wt %, based on the total oxygenates, of glycols by flashing; and
   (vii) recovering glycols from the glycol rich stream.

2. The process of claim 1 wherein further comprising (viii) recycling at least a portion of said monooxygenates stream to the first reaction system.

3. The process of claim 1 wherein glycols are recovered by separating finished glycol from the glycol rich stream.

4. The process of claim 1 wherein the glycol content of the hydrogenolysis stream produced in step (ii) is at least 15 wt % based on the total oxygenates content.

5. The method process of claim 1 wherein the ratio of the hydrogenolysis stream provided to the first separation system and to the second reaction system is in the range of 1.5:1 to 10:1.

6. The process of claim 1 wherein the maximum steady state temperature of the first reaction system is at least 10° C. less than the maximum steady state temperature of the second reaction system;

7. The process of claim 6 wherein no process heat from external source is added between the first and second reaction systems, or to the second reaction system, wherein the temperature increase in the second reaction system results from the exothermic heats from the first reaction system and the second reaction system.

8. The process of claim 4 wherein the glycol rich stream in step (vi) comprises at least 25 wt %, based on the total oxygenates, of glycols.

9. The process of claim 1 wherein bio-based feedstock is subjected to a digestive solvent to provide bio-based feedstock stream comprising carbohydrates and water.

10. The process of claim 1 wherein the conversion of carbohydrate in the first reaction system is limited to less than 80%.

11. The method process of claim 10 wherein the conversion of carbohydrate in the first reaction system is limited to less than 70%.

12. The process of claim 11 wherein the conversion of carbohydrate in the first reaction system is limited to less than 60%.

13. The method process of claim 12 wherein the conversion of carbohydrate in the first reaction system is limited to less than 50%.

14. The process of claim 1 wherein the conversion of carbohydrates to monooxygenated compounds across the first reaction system and the second reaction system is less than 90%.

15. The process of claim 14 wherein the oxygenated intermediate stream from the second reaction system is flash distilled to provide a stream containing at least a portion of monooxygenate intermediates as feed for production of liquid fuels.

16. The process of claim 15 wherein the bottoms from flashing containing enriched concentrations of unconverted carbohydrates, sugar alcohols, glycols, and some monooxygenates, are recycle to the first reaction system.

17. A method process of co-producing biofuels and glycols comprising:
  (i) providing a bio-based feedstock;
  (ii) contacting the bio-based feedstock with a digestive solvent to provide a bio-based feedstock stream containing carbohydrates and water;
  (iii) contacting, in a first reaction system, the bio-based feedstock stream with hydrogen in the presence of a hydrogenolysis catalyst at a temperature in the range of 120° C. to 280° C. and 0.1 to 150 bar of hydrogen to produce a hydrogenolysis stream containing at least 5 wt %, based on the total oxygenates content, of glycols that comprises ethylene glycol (EG) and 1,2-propylene glycol (PG), and other monooxygenates;
  (iv) contacting, in a second reaction system, at least a first portion of said hydrogenolysis stream with hydrogen in the presence of a hydrogenolysis catalyst at a temperature in the range of 160 ° C. to 280 ° C. and in the presence of 0.1 to 150bar hydrogen to produce an oxygenated intermediate stream comprising at least 5 wt %, based on the total oxygenates, of monooxygenated hydrocarbons of chain length less than 6 carbons;
  (v) processing at least a portion of the oxygenated intermediate stream to form a liquid fuel;
  (vi) providing a second portion of said hydrogenolysis stream to a first separation system;
  (vii) separating a portion of said hydrogenolysis stream, in the first separation system, to a monooxygenates stream comprising monooxygenates and a glycol rich stream comprising at least 10 wt %, based on the total oxygenates, of glycols by flashing; and
  (viii) recovering glycols from the glycol rich stream.

18. The process of claim 17 wherein further comprising (ix) recycling at least a portion of said monooxygenates stream to the first reaction system.

19. The process of claim 17 wherein glycols are recovered by separating finished glycol from the glycol rich stream.

20. The process of claim 17 wherein the oxygenated intermediates is subjected to condensation to produce a liquid fuel.

21. The process of claim 17 wherein the oxygenated intermediates is subjected to dehydration and alkylation to produce a liquid fuel.

22. A process of co-producing biofuels and glycols comprising:
  (i) providing a bio-based feedstock stream containing carbohydrates and water;
  (ii) contacting, in a first reaction zone, the bio-based feedstock stream with hydrogen in the presence of a hydrogenolysis catalyst at a temperature in the range of 120° C. to 280° C. and 0.1 to 150 bar of hydrogen to produce a hydrogenolysis intermediate containing at least 5 wt %, based on the total oxygenates content, of glycols that comprises ethylene glycol (EG) and 1,2-propylene glycol (PG), and other monooxygenates;
  (iii) contacting, in a second reaction zone, said hydrogenolysis intermediate with hydrogen in the presence of a hydrogenolysis catalyst at a temperature in the range of 160° C. to 280° C. and in the presence of 0.1 to 150 bar hydrogen to produce a combined glycol and oxygenated intermediate stream comprising at least 5 wt %, based on the total oxygenates, of monooxygenated hydrocarbons of chain length less than 6 carbons, and greater than 5 wt % glycols;
  (iv) separating, by flashing, the combined glycol and oxygenated intermediate stream into a glycol rich stream comprising at least 10 wt %, based on the total oxygenates, of glycols, and a mono-oxygenates-rich stream;
  (v) processing at least a portion of the monooxygenates-rich stream to form a liquid fuel; and
  (vi) recovering glycols from the glycol rich stream.

23. The process of claim 22 where the temperature of the second reaction zone is at least 10° C. higher than the temperature of the first reaction zone.

24. The process of claim 22 where at portion of either or both of the glycol-rich stream or mono-oxygenates rich stream is recycled to provide solvent for the first reaction zone.

25. The process of claim 24 where the recycled solvent is routed to a digestion zone to digest solid biomass to provide feed for the first reaction zone.

* * * * *